(12) United States Patent
Inoue et al.

(10) Patent No.: US 10,085,626 B2
(45) Date of Patent: Oct. 2, 2018

(54) IN-VIVO MONITORING CAMERA SYSTEM, AND SUPPORT TUBE FOR IN-VIVO MONITORING CAMERA SYSTEM

(71) Applicant: Sharp Kabushiki Kaisha, Osaka-shi, Osaka (JP)

(72) Inventors: Tsuguhisa Inoue, Osaka (JP); Toshihisa Gotoh, Osaka (JP); Kishoh Takamatsu, Osaka (JP); Kei Urakawa, Osaka (JP); Hitoshi Aoki, Osaka (JP)

(73) Assignee: Sharp Kabushiki Kaisha, Sakai (JP)

( * ) Notice: Subject to any disclaimer, the term of this patent is extended or adjusted under 35 U.S.C. 154(b) by 0 days.

(21) Appl. No.: 15/031,777

(22) PCT Filed: Nov. 26, 2014

(86) PCT No.: PCT/JP2014/081225
§ 371 (c)(1),
(2) Date: Apr. 25, 2016

(87) PCT Pub. No.: WO2015/080148
PCT Pub. Date: Jun. 4, 2015

(65) Prior Publication Data
US 2016/0242635 A1    Aug. 25, 2016

(30) Foreign Application Priority Data
Nov. 26, 2013    (JP) .................. 2013-244151

(51) Int. Cl.
*A61B 1/05*    (2006.01)
*G02B 23/24*    (2006.01)
(Continued)

(52) U.S. Cl.
CPC ............ *A61B 1/05* (2013.01); *A61B 1/00045* (2013.01); *A61B 1/00114* (2013.01);
(Continued)

(58) Field of Classification Search
CPC ... A61B 1/05; A61B 1/00114; A61B 1/00045; A61B 1/0661; A61B 1/045;
(Continued)

(56) References Cited

U.S. PATENT DOCUMENTS

2005/0197536 A1* 9/2005 Banik ................ A61B 1/00059
600/179
2006/0074307 A1 4/2006 Igarashi et al.
(Continued)

FOREIGN PATENT DOCUMENTS

JP    5-34605 A    2/1993
JP    2005-319086 A    11/2005
(Continued)

OTHER PUBLICATIONS

Aoki et al., "Camera System for Monitoring Inside of Body", U.S. Appl. No. 15/546,291, filed Jul. 26, 2017.
(Continued)

*Primary Examiner* — Sathyanaraya V Perungavoor
*Assistant Examiner* — Howard D Brown, Jr.
(74) *Attorney, Agent, or Firm* — Keating & Bennett, LLP

(57) ABSTRACT

An in-vivo monitoring camera system that includes: a camera support tube (13) of which one end part is introduced into a body; a camera unit (11) which joins with the camera support tube in the body; a joining portion which joins the camera unit and the support tube to each other; a camera side cable (12) which is connected to the camera unit, and is drawn out toward the outside of the body through the camera support tube; a control system which is on the outside of the body, is connected to the camera side cable, and includes at least a display apparatus; and a cooling system (77) which cools the camera support tube to which heat of the imaging unit is transferred.

15 Claims, 13 Drawing Sheets

(51) Int. Cl.
*A61B 1/00* (2006.01)
*A61B 1/06* (2006.01)
*A61B 1/313* (2006.01)
*A61B 1/12* (2006.01)
*A61B 1/045* (2006.01)
*H04N 5/225* (2006.01)
*A61B 17/00* (2006.01)
*A61B 90/00* (2016.01)

(52) U.S. Cl.
CPC ...... *A61B 1/00128* (2013.01); *A61B 1/00147* (2013.01); *A61B 1/045* (2013.01); *A61B 1/053* (2013.01); *A61B 1/0661* (2013.01); *A61B 1/0676* (2013.01); *A61B 1/0684* (2013.01); *A61B 1/128* (2013.01); *A61B 1/313* (2013.01); *G02B 23/2484* (2013.01); *H04N 5/2252* (2013.01); *H04N 5/2256* (2013.01); *A61B 90/361* (2016.02); *A61B 2017/00283* (2013.01); *H04N 2005/2255* (2013.01)

(58) Field of Classification Search
CPC . A61B 1/00147; A61B 1/128; A61B 1/00128; A61B 1/313; A61B 1/0684; A61B 1/0676; A61B 1/053; H04N 5/2252; H04N 5/2256
See application file for complete search history.

(56) References Cited

U.S. PATENT DOCUMENTS

| | | | | |
|---|---|---|---|---|
| 2008/0309758 | A1* | 12/2008 | Karasawa | A61B 1/00114 348/65 |
| 2009/0253957 | A1* | 10/2009 | Yasunaga | A61B 1/05 600/109 |
| 2010/0033559 | A1* | 2/2010 | Yasunaga | A61B 1/05 348/65 |
| 2010/0113872 | A1 | 5/2010 | Asada et al. | |
| 2010/0160813 | A1* | 6/2010 | Ohno | A61B 1/00105 600/562 |
| 2011/0046440 | A1* | 2/2011 | Asada | A61B 1/00147 600/104 |
| 2012/0316575 | A1 | 12/2012 | Farin et al. | |
| 2014/0005474 | A1* | 1/2014 | Farin | A61B 1/00154 600/104 |
| 2014/0027270 | A1* | 1/2014 | Valls Angles | B29C 33/04 204/196.01 |

FOREIGN PATENT DOCUMENTS

| | | |
|---|---|---|
| JP | 2008-80117 A | 4/2008 |
| JP | 2009-72368 A | 4/2009 |
| JP | 2009-82700 A | 4/2009 |
| JP | 4472727 B2 | 6/2010 |
| JP | 4599474 B1 | 12/2010 |
| JP | 2013-538102 A | 10/2013 |
| WO | 2015/020124 A1 | 2/2015 |

OTHER PUBLICATIONS

Gotoh et al., "In-Body Monitoring Camera System and Support Tube for In-Body Monitoring-Camera-System", U.S. Appl. No. 14/899,269, filed Dec. 17, 2015.

Urakawa et al., "Intracorporeal-Monitoring Camera System, Support Tube for Intracorporeal-Monitoring Camera System, and Cable Holder for Intracorporeal-Monitoring Camera System", U.S. Appl. No. 14/917,064, filed Mar. 7, 2016.

Urakawa et al., "Camera System for Monitoring Inside of Body, Accessory for Support Tube of Camera System for Monitoring Inside of Body, Fixing Tool for Camera System for Monitoring Inside of Body, and Method for Installing Camera System for Monitoring Inside of Body", U.S. Appl. No. 15/031,816, filed Apr. 25, 2016.

Aoki et al., "Camera System for Monitoring Inside of Body and Auxiliary Device and Method for Installing Imaging Apparatus for Monitoring Inside of Body", U.S. Appl. No. 15/111,514, filed Jul. 14, 2016.

Aoki et al., "In-Body Monitroing Camera System and Camera Unit", U.S. Appl. No. 15/129,044, filed Sep. 26, 2016.

Aoki et al., "Camera System for Monitoring Inside of Body and Auxiliary Tool Set", U.S. Appl. No. 15/112,726, filed Jul. 20, 2016.

* cited by examiner

11: CAMERA UNIT
12: CAMERA SIDE CABLE
13: CAMERA SUPPORT TUBE
15: CABLE CONNECTOR
16: INSTRUMENT SIDE CABLE
17: CAMERA UNIT CONTROL INSTRUMENT
18: DISPLAY
31: CANNULA
32a TO 32c: TROCAR
33a TO 33c: FORCEPS
34: ENDOSCOPE
41: ABDOMINAL WALL
42: ORGAN
117: CAMERA UNIT CONTROL INSTRUMENT
118: DISPLAY

11: CAMERA UNIT
12: CAMERA SIDE CABLE
13: CAMERA SUPPORT TUBE
14: SUPPORT TUBE JOINING PORTION
19: CIRCUIT BOARD
21: CAMERA HOUSING
22: GRIPPING PORTION
25: SOLID-STATE IMAGING DEVICE
26: LENS
27: ILLUMINATION APPARATUS
28: CONTROL CIRCUIT
49: THERMAL CONDUCTOR

11: CAMERA UNIT
12: CAMERA SIDE CABLE
13: CAMERA SUPPORT TUBE
31: CANNULA
41: ABDOMINAL WALL
43: HEAT SINK
46: HEAT RADIATION FAN
77: COOLING SYSTEM

11: CAMERA UNIT
12: CAMERA SIDE CABLE
13: CAMERA SUPPORT TUBE
31: CANNULA
40: LOW TEMPERATURE MATERIAL (COOLING MATERIAL)
41: ABDOMINAL WALL
44: LOW TEMPERATURE MATERIAL ATTACHING PLATE
77: COOLING SYSTEM

11: CAMERA UNIT
12: CAMERA SIDE CABLE
13: CAMERA SUPPORT TUBE
31: CANNULA
41: ABDOMINAL WALL
43: HEAT SINK
44: LOW TEMPERATURE MATERIAL ATTACHING PLATE
45: PELTIER ELEMENT
46: HEAT RADIATION FAN
47, 48: PELTIER ELEMENT CABLE
77: COOLING SYSTEM

IN-VIVO MONITORING CAMERA SYSTEM, AND SUPPORT TUBE FOR IN-VIVO MONITORING CAMERA SYSTEM

TECHNICAL FIELD

The present invention relates to an in-vivo monitoring camera system which is provided with an in-vivo monitoring camera that can be introduced into a body, and a support tube for an in-vivo monitoring camera system.

BACKGROUND ART

Endoscopic surgery is minimally invasive surgery for performing examination or medical treatment without laparotomy with respect to a patient. In the endoscopic surgery, a treatment tool, such as forceps, and an endoscope are separately guided toward the inside of a body cavity of the patient, and a practitioner captures an image of a tip end part of the treatment tool inserted into the body cavity within an observation visual field of the endoscope, and performs the treatment operation while observing a treatment state of the patient by the treatment tool using the endoscope. In the endoscopic surgery, the treatment tool and the endoscope are guided toward the inside of the body cavity through a pipe punctured through a body wall (for example, an abdominal wall) in an abdomen or the like of the patient. In addition, the pipe is a tube-like member which is a so-called trocar.

The practitioner enlarges the image by making the endoscope approach an organ, and performs incision or suturing of the organ, but at this time, the visual field of the practitioner becomes extremely narrow. Therefore, an in-vivo monitoring camera which can widely grasp a state (for example, the movement of the treatment tool, a bleeding state, and a remaining state of a residual, such as gauze, outside a work region) outside the work region, has been called for.

Corresponding to such a demand, in PTL 1, an apparatus which directly inserts a needle-like connector electrode into an abdominal wall, and joins the connector electrode and a camera main body (in-vivo monitoring camera) to each other in a body, is disclosed.

In PTL 2, an apparatus which inserts a camera unit (in-vivo monitoring camera) and a communication cable which joins with the camera unit from a trocar, draws out a needle and the communication cable from an abdominal wall hole toward the outside of a body in a state where an end part of the communication cable is hooked to the needle inserted from the abdominal wall hole, and fixes the communication cable, is disclosed.

CITATION LIST

Patent Literature

PTL 1: Japanese Patent No. 4472727 (issued on Jun. 2, 2010)
PTL 2: Japanese Patent No. 4599474 (issued on Dec. 15, 2010)

SUMMARY OF INVENTION

Technical Problem

An object of the in-vivo monitoring camera is to grasp a state outside an observation visual field of the endoscope in the endoscopic surgery. Therefore, it is necessary to reduce the size of the camera not to interrupt the surgery.

In a case where the size of the in-vivo monitoring camera is small, discharge of heat generated from the in-vivo monitoring camera is a problem. It is assumed that the in-vivo monitoring camera is fixed to an abdominal wall. Therefore, it is necessary that the temperature of the in-vivo monitoring camera is the temperature which does not cause a low-temperature burn of the abdominal wall due to the heat generated inside the in-vivo monitoring camera.

However, in order to maintain the temperature of a surface of the in-vivo monitoring camera which has a possibility of coming into contact with the abdominal wall to be low, when forming the surface of the in-vivo monitoring camera by a material having low thermal conductive properties, it is difficult to effectively discharge the heat generated inside the in-vivo monitoring camera. Therefore, there is a problem that the temperature of the inside of the in-vivo monitoring camera becomes high and desirable performance cannot be obtained due to the heat generated from an imaging element inside the in-vivo monitoring camera and a light-emitting element used for illumination, and there is a concern about failure.

In consideration of the above-described problems, an object of the present invention is to provide an in-vivo monitoring camera system which can effectively discharge heat generated inside the in-vivo monitoring camera.

Solution to Problem

In order to solve the above-described problems, there is provided an in-vivo monitoring camera system according to an aspect of the present invention, including: a support tube for which one end part is introduced into a body; an imaging unit which joins with the support tube in the body; a joining portion which joins the imaging unit and the support tube to each other; a cable which is connected to the imaging unit, and is drawn out toward the outside of the body through the support tube; a control system which is on the outside of the body, is connected to the cable, and includes at least a display apparatus; and a cooling system which cools the support tube to which heat of the imaging unit is transferred.

Advantageous Effects of Invention

According to one aspect of the present invention, it is possible to lower the temperature of an imaging unit by cooling a support tube to which heat of the imaging unit is transferred.

DESCRIPTION OF EMBODIMENTS

Figure 1:
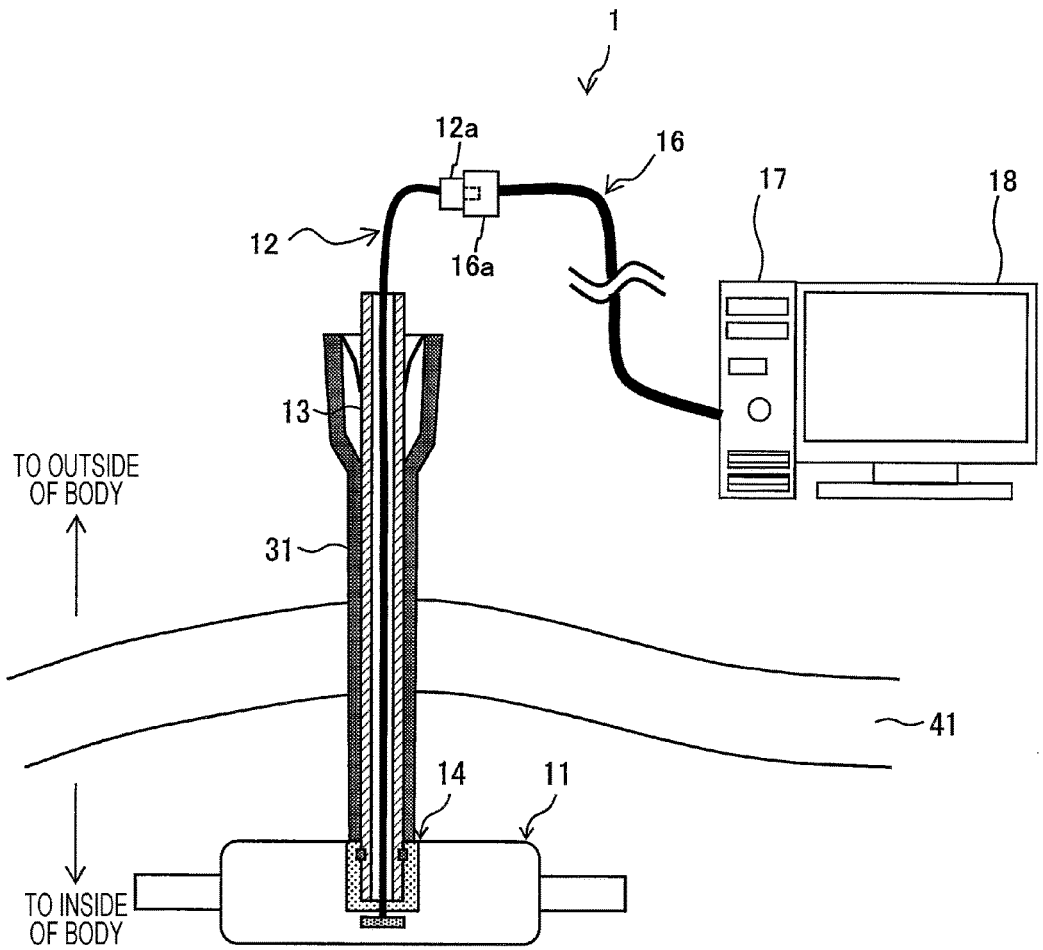
FIG. 1 is a schematic view illustrating a configuration of an in-vivo monitoring camera system according to Embodiment 1.

An embodiment of the present invention will be described based on FIGS. 1 to 13 as follows. For convenience of description, members having the same functions as those of members illustrated in each embodiment will be given the same reference numerals, and detailed descriptions thereof will be appropriately omitted. In addition, the dimensions, such as the shape, the length, the size, and the width, of configurations described in each drawing do not reflect the real shape or dimensions, and are appropriately changed for making the drawings apparent and simple.

[Embodiment 1]

(Schematic Configuration of In-vivo Monitoring Camera System 1)

FIG. 1 is a schematic view illustrating a configuration of an in-vivo monitoring camera system 1 according to Embodiment 1. As illustrated in FIG. 1, the in-vivo monitoring camera system 1 includes a camera unit 11 (imaging unit), a camera side cable 12 of which one end is connected to the camera unit 11, a camera support tube 13 (support tube), a control system including a camera unit control instrument 17 and a display 18 (display apparatus), an instrument side cable 16 of which one end is connected to the camera unit control instrument 17. In addition, as a camera side cable connector 12a provided at the other end of the camera side cable 12, and an instrument side cable connector 16a provided at the other end of the instrument side cable 16, are fitted to each other, the camera unit 11 and the control system 3 are electrically connected to each other. Hereinafter, the camera side cable connector 12a will be referred to as a connector 12a, and the instrument side cable connector 16a will be referred to as a connector 16a.

One end part of the camera support tube 13 is guided toward the inside of the body through the inside of a cannula 31 (tube-like device, holding tube) punctured through an abdominal wall. The camera unit 11 performs imaging inside the body, and is guided toward the inside of the body through the tube-like member which is called a trocar. In addition, in a state where the camera side cable 12 passes through the inside of the camera support tube 13, one end part (inside the body) of the camera support tube 13 and the camera unit 11 inside the body join with each other at a support tube joining portion 14 (joining portion).

In FIG. 1, by inserting a pin part of the male-shaped (projected) camera side cable connector 12a into the female-shaped (recessed) instrument side cable connector 16a, the connectors 12a and 16a are fitted to each other. However, a configuration in which the male-shaped connector and the female-shaped connector is reversed, or in which the female-shaped camera side cable connector and the male-shaped instrument side cable connector is fitted to each other, may be employed. In addition, in the female-shaped (recessed) camera side cable connector, since the pin part is not exposed to the outside similar to the male-shaped connector, staining is unlikely to occur on a terminal unit even in a case where the connector incorrectly touches the inside of the body. Accordingly, it is desirable that the female-shaped (recessed) connector is used for the camera side cable.

Although will be described later in detail, when the camera unit 11 and the camera support tube 13 are connected to each other, the camera side cable 12 (including the connector 12a) is drawn out toward the outside of the body from the inside of the body through the camera support tube 13. Therefore, an outer diameter of the camera side cable connector 12a is smaller than an outer diameter of the camera support tube 13. In other words, when reducing the outer diameter of the camera side cable connector 12a, it is possible to reduce the outer diameter of the camera support tube 13. Accordingly, a special effect is achieved in which low invasiveness is improved. In other words, it is desirable to make the outer diameter of the camera side cable connector 12a as small as possible. For example, as illustrated in FIG. 1, it is desirable that the outer diameter of the camera side cable connector 12a is equal to or smaller than the outer diameter of the instrument side cable connector 16a, and that the outer diameter (cable diameter) of the camera side cable 12 is smaller than the outer diameter (cable diameter) of the instrument side cable 16.

In addition, it is possible to provide a slit which reaches from one end to the other end of the camera support tube. In this case, the camera side cable 12 passes through the inside of the camera support tube via the slit from the side surface of the camera support tube. Accordingly, it becomes easy to make the camera side cable (including the connector) pass through the camera support tube, and a cooling effect of the camera support tube, such as improvement of ventilation properties in the camera support tube due to the slit, is also achieved. From the viewpoint of the cooling effect, it is possible to provide a ventilation port at a part (in particular, a part which protrudes from a tip end of the cannula in a case where the camera support tube passes through the cannula) which is on outside of the body of the camera support tube.

Because the slit is provided, since it is not necessary for the camera side cable connector 12a to pass through the inside of the camera support tube 13, it is possible to reduce the inner diameter of the camera support tube 13 to be smaller than the dimension of the outer diameter of the camera side cable connector 12a. Due to this, if the thickness of the camera support tube 13 is the same, it is possible to further reduce the outer diameter of the camera support tube 13. Accordingly, a special effect is achieved in which low invasiveness is further improved.

In FIG. 1, in order to make the drawing easy to understand, it is described that an outer diameter of the camera side cable connector 12a is greater than an actual outer diameter, and an outer diameter (cable diameter) of the camera side cable 12 is smaller than an actual outer diameter. As described above, in practice, the outer diameter of the camera side cable connector 12a is smaller than the outer diameter of the camera support tube 13. Furthermore, one pin of the camera side cable connector 12a is illustrated for making the drawing simple, but generally, a plurality of pins are configured according to the number of electric wires used for the cable. This is also employed in other drawings.

As will be described later, since the camera side cable 12 (including the connector 12a) returns to the inside of the body during the withdrawing of the camera unit 11, it is necessary to maintain the instrument side cable connector 16a which is in contact with the camera side cable 12 and a part having a predetermined length from the instrument side cable connector 16a to be clean, in the instrument side cable 16.

According to the above-described connection, an image captured by the camera unit 11 is sent to the camera unit control instrument 17, and a control signal from the camera unit control instrument 17 is sent to the camera unit 11.

By employing the system configuration described above, since a wired type is employed in transmission from the camera unit 11 to the camera unit control instrument 17, it is possible to increase a transmission speed, and to stabilize and send/receive the signal, and thus, it is possible to obtain an image having high resolution. In addition, it is possible to perform communication at low power compared to a wireless type, and to decrease the size of the camera unit 11 by supplying power from the outside. Therefore, since it is possible to reduce damage when the camera unit 11 is guided toward the inside of the body due to the small size, there is an effect that low invasiveness is improved.

The camera unit control instrument 17 displays the image sent from the camera unit 11 on the display 18, and sends the control signal to the camera unit 11. The camera unit control instrument 17 and the display 18 may be integrally configured, and may be separately configured.

(Configuration of Imaging Apparatus)

FIG. 2(a) is a schematic sectional view of the camera unit 11 of Embodiment 1. FIG. 2(b) is an upper view thereof. As illustrated in FIGS. 2(a) and 2(b), in the camera unit 11, inside a camera housing 21 (imaging housing), a circuit board 19, and a solid-state imaging device 25, a control circuit 28, an illumination apparatus 27, and a lens 26, which are connected to the circuit board 19, are provided. On an upper surface of the camera housing 21, the recessed support tube joining portion 14 is provided. The support tube joining portion 14 has an annular opening hole structure, and includes a locking claw 23 (projected part) on an inner wall thereof. In addition, a gripping portions 22 protrude from each of both opposing side surfaces in the camera housing 21. The gripping portion 22 is gripped when the camera unit 11 is guided toward the inside of the camera support tube 13 by using forceps, and when the camera unit 11 and the camera support tube 13 join with each other, an upper surface (surface provided with the support tube joining portion 14) of the camera unit 11 is gripped to face an end part of the camera support tube 13.

The camera side cable 12 is connected to the circuit board 19, and is guided toward the outside of the camera unit 11 to pass through the inside of the support tube joining portion 14. A connection part of the circuit board 19 and the camera side cable 12 is sealed by a resin or the like. Since the camera side cable 12 is led into the body cavity through the trocar, the camera side cable 12 is formed of a flexible material. Furthermore, at a part (bottom unit of the recessed support tube joining portion 14) which is drawn out in the camera side cable 12 inside the support tube joining portion 14, the camera side cable 12 is adhered and fixed to the support tube joining portion 14. An example of the adhesion and fixing includes sealing and fixing by an adhesive or an O ring. Intrusion of water and mixing of foreign materials into the camera unit 11 from the adhered and fixed part, are prevented.

As will be described later, since the camera side cable 12 is guided toward the inside of a body cavity through the tube-like member, such as the trocar, in a state of being connected to the camera unit 11, or is drawn out toward the outside of the body through the camera support tube 13, the camera side cable 12 is formed of a flexible material having flexibility.

Examples of the solid-state imaging device 25 (imaging element) include a charge coupled device (CCD) and a complementary metal-oxide semiconductor (CMOS) image sensor. The solid-state imaging device 25 and the lens 26 configure an imaging unit 24.

Figure 2:
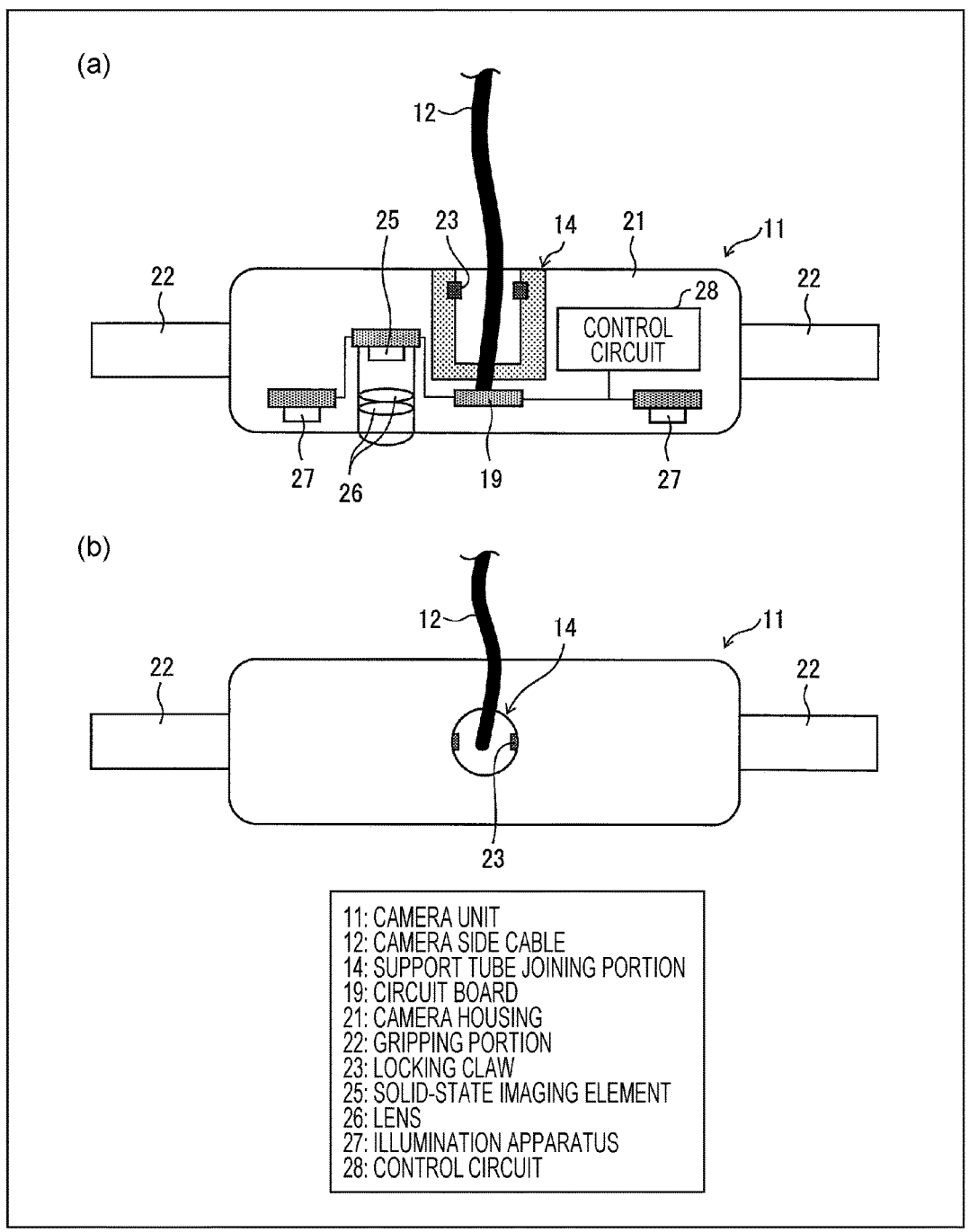
FIG. 2(a) is a schematic sectional view of a camera unit according to Embodiment 1.
FIG. 2(b) is an upper view thereof.

The illumination apparatus 27 makes an image captured by the camera unit 11 clear by illuminating the inside of the body with light. It is preferable that the size of the illumination apparatus 27 is small, and a light emitting diode (LED) or the like can be appropriately used. In addition, as illustrated in FIG. 2, a plurality of illumination apparatuses 27 may be provided in the camera unit 11.

In addition, in the camera housing 21 of the camera unit 11, a part at which the lens 26 or the illumination apparatus 27 is disposed is configured of a transparent material, but it is desirable that a region other than the part is configured of a cool-colored material, such as a blue, blue-green, or green material, which is easily noticed inside the body. In addition, it is more desirable that a film of the surface of the camera side cable 12 is configured of a blue, blue-green, or green material. Furthermore, it is desirable that the cable connector is also configured of a similarly colored material. In this manner, by making a color inside a body which is red or yellow into a cool color, such as blue, blue-green, or green color that is a complementary color, it is possible to make visual recognition easy during installation work or withdrawing work inside the body, which will be described later. For example, even when the camera unit 11 is incorrectly dropped in the body and is hidden by the shade of the organ, since the camera side cable 12 is longer compared to the camera unit 11, there are more cases where the camera unit 11 is seen at a location which can be visually recognized, and can be immediately found. Accordingly, by coloring the camera side cable 12 in blue, blue-green, or green, a special effect is achieved in which the time of the installation work of the camera unit 11 can be shortened and safety is also improved. In this manner, in coloring the camera unit 11 or the camera side cable 12, it is possible to use a color (a color which is easily seen in the body) that corresponds to visible light having a wavelength of 420 nm to 570 nm (preferably, 450 nm to 530 nm).

As described above, other than coloring with a blue or green material, a phosphorescent material or a reflecting material which is likely to be visually recognized may be used. In this manner, since it is possible to immediately find the camera unit 11 even when the camera unit 11 is in the shade of an organ that is unlikely to be visually recognized, or at an end of a visual field where illumination light is unlikely to reach, the phosphorescent material or the reflecting material is particularly effective.

(Structure of Camera Support Tube 13)

Figure 3:
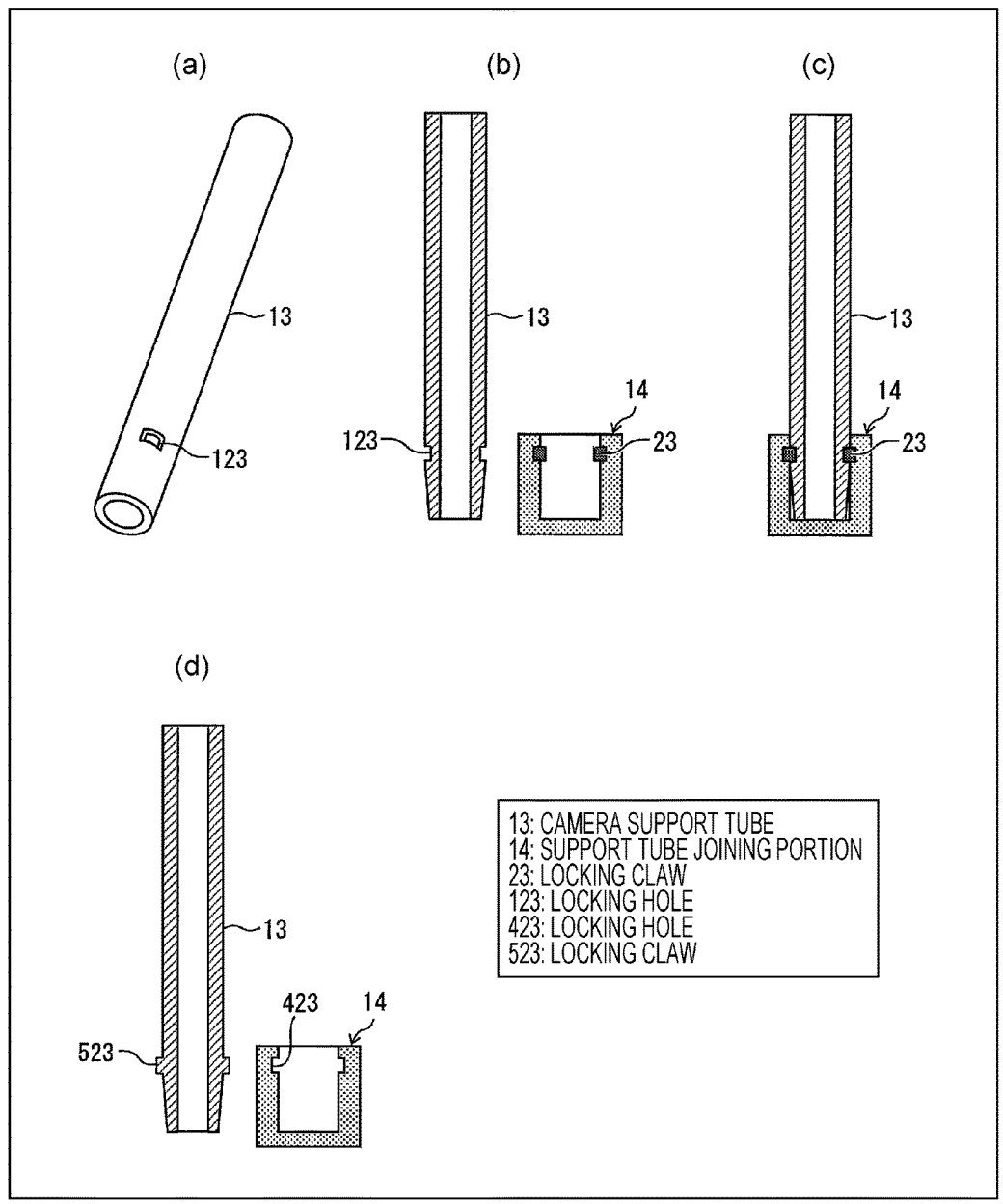
FIG. 3(a) is a perspective view of a camera support tube for FIG. 1.
FIG. 3(b) is a sectional view of the camera support tube and a support tube joining portion of FIG. 1.
FIG. 3(c) is a sectional view illustrating a joined state of the camera support tube and the support tube joining portion of FIG. 1.
FIG. 3(d) is a sectional view illustrating a modification example of the camera support tube and the support tube joining portion.
Figure 4:
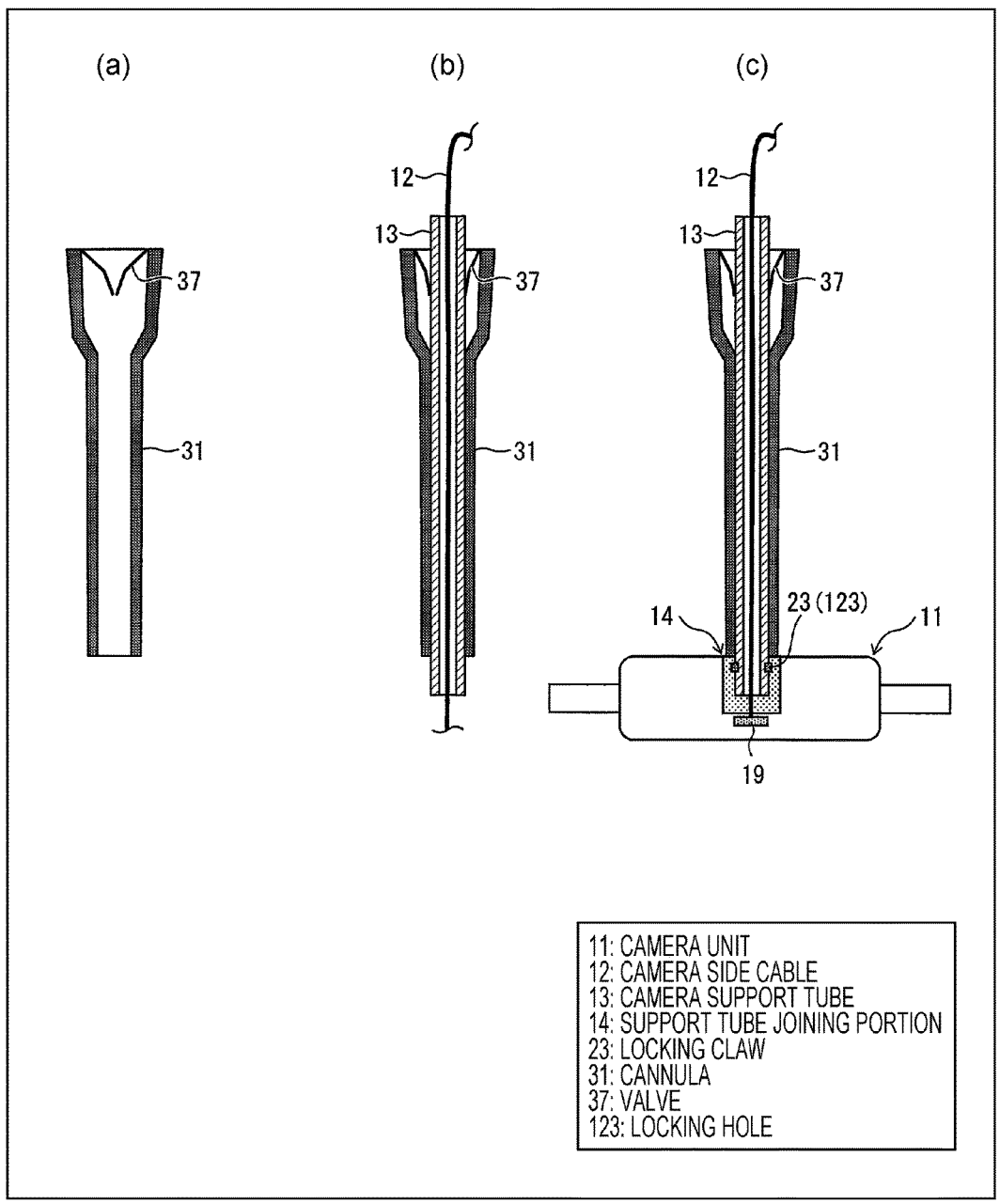
FIG. 4(a) is a sectional view illustrating a structure of a cannula.
FIG. 4(b) is a sectional view illustrating a state where the camera support tube of FIG. 3 is inserted into the cannula.
FIG. 4(c) is a sectional view illustrating a joined state of the camera support tube inserted into the cannula and a camera unit of FIG. 2.
Figure 5:
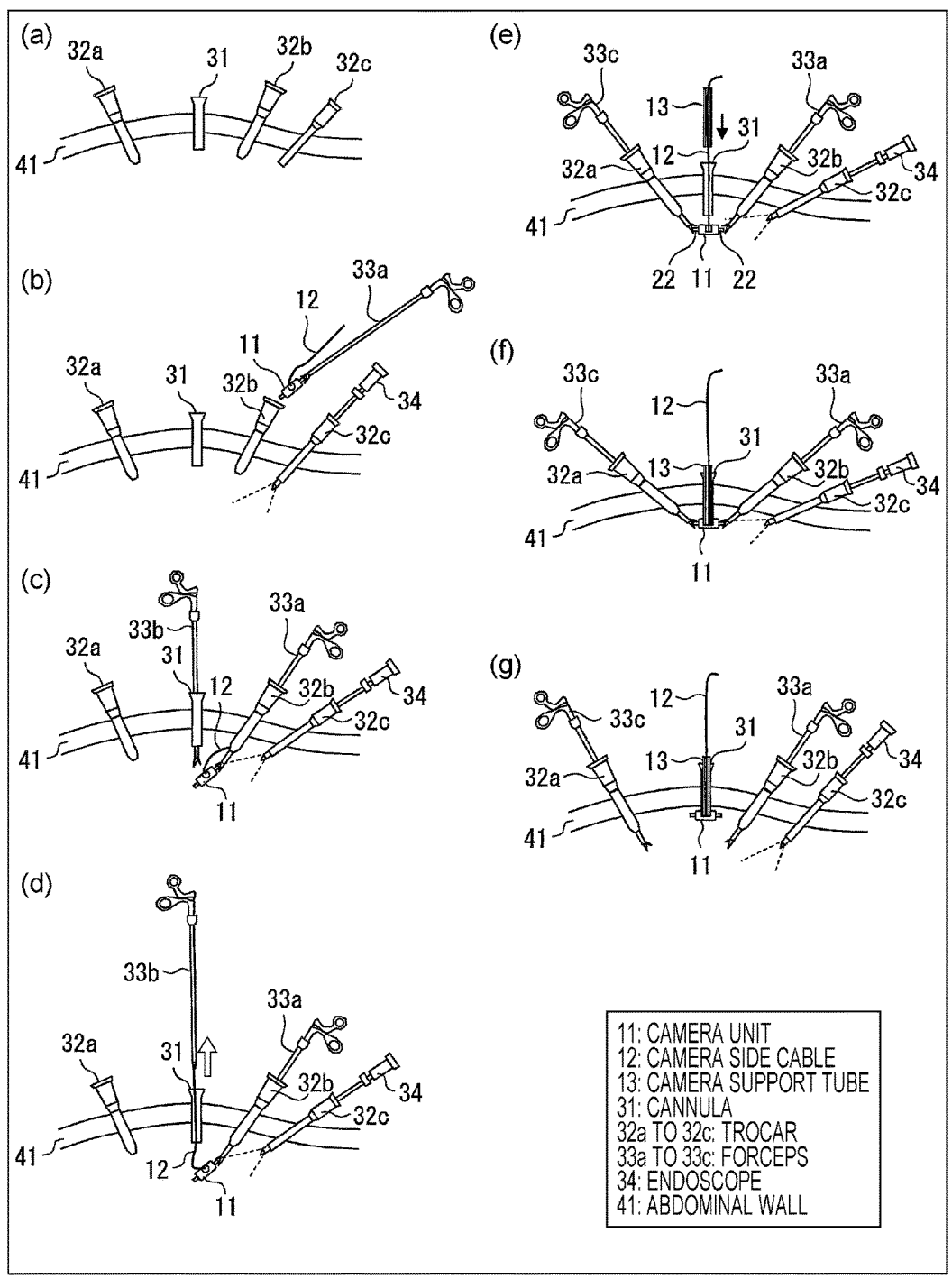
FIGS. 5(a) to 5(g) are schematic views illustrating a method for installing a camera unit in a body according to Embodiment 1.

FIG. 3 illustrates a schematic structure of the camera support tube 13 and the support tube joining portion 14. FIG. 3(a) is a perspective view of the camera support tube 13. The camera support tube 13 is a support tube which supports the camera unit 11 by joining the camera support tube 13 to the camera unit 11 inside the body in a state where the camera side cable 12 is drawn out toward the outside of the body through the inside of the camera side cable 12. One end part of the camera support tube 13 is guided toward the inside of the body through a body wall 41, such as the abdominal wall. The end part guided toward the inside of the body joins with the camera unit 11 by the support tube joining portion 14.

As illustrated in FIG. 3(a), the camera support tube 13 is a cylindrical tube, and has a locking hole 123 (recessed part) at an end part on a side to which is guided toward the inside of the body. From the viewpoint of joining strength with the camera unit 11 (FIG. 1), the camera support tube 13 is formed of a hard material. The material of the camera support tube 13 is not particularly limited if the material has rigidity which can obtain the joining strength that can stably support the camera unit 11, and which can fix the camera unit 11 at a desirable position and orientation. For example, stainless steel, ceramics (fine ceramics), or reinforced plastic may be used.

The camera support tube 13 is strong to a physical impact since the camera support tube 13 has a cylindrical shape, and it is easy to combine the camera support tube 13 with a general cannula, which is the same cylindrical tube. In addition, a tip end of the camera support tube 13 is sharpened, or is diagonally cut in a round shape similar to a needle, and may also be used as a puncturing device.

FIG. 3(b) is a sectional view of the camera support tube 13 and the support tube joining portion 14. FIG. 3(c) is a sectional view illustrating a state where the camera support tube 13 is inserted into the support tube joining portion 14. As illustrated in FIGS. 3(b) and 3(c), since the tip part of the camera support tube 13 has more tapered shape than the locking hole 123, the tip end (inside the body) of the camera support tube 13 is not hooked to the locking claw 23 of the support tube joining portion 14, and when pushing the camera support tube 13 until the tip end thereof reaches a deep part of the support tube joining portion 14, the locking hole 123 is fitted to the locking claw 23. In addition, the camera support tube 13 is not limited to the above-described structure. Both end parts of the camera support tube 13 may have the same thickness as each other.

In this manner, in a case where the tip end part of the camera support tube 13 has a tapered shape in order to make the camera support tube 13 easy to be inserted, it is possible to have a tapered shape by making the thickness of the camera support tube 13 thin. At this time, it is more desirable that the inner diameter of the camera support tube 13 is constant, and only an outer diameter of the camera support tube 13 is changed (the size of the external shape is reduced toward the tip end), since there is not case where the instrument is hooked in the middle (at a narrowed location) and does not fall out when inserting the instrument into the camera support tube.

As illustrated in FIG. 3(d), it is possible to provide a locking claw 523 in the camera support tube 13, and to provide a locking hole 423 in the support tube joining portion 14.

In addition, a groove-like recessed part 132 which goes round an outer side surface illustrated in FIGS. 12(a) and 12(b) may be provided at the end part of the camera support tube 13, and a ridge-like projected part 232 which goes round an inner side surface may be provided in the opposing support tube joining portion 14. In addition, a ridge-like projected part which goes round the outer side surface may be provided at the end part of the camera support tube 13, and a groove-like recessed part which goes round the inner side surface may be provided in the opposing support tube joining portion 14. This manner is more desirable since it is not necessary to perform an operation of matching positions of the locking hole and the locking claw when inserting the camera support tube 13, the joining of the hole and the claw becomes easy, and the joining strength also increases.

(Inserting Camera Support Tube 13 into Cannula 31 and Joining Camera Support Tube 13 to Camera Unit 11)

FIG. 4(a) is a sectional view of the cannula 31. FIG. 4(b) is a sectional view illustrating a state where the camera support tube 13 illustrated in FIGS. 3(a) to 3(d) is inserted into the cannula 31 illustrated in FIG. 4(a). FIG. 4(c) is a sectional view illustrating a joined state of the camera support tube 13 inserted into the cannula 31 and the camera unit 11 illustrated in FIG. 2.

As illustrated in FIG. 4(a), when the cannula 31 is a tube-like device, one end part (outside the body) is thicker than the other end part (inside the body), and the cannula 31 is inserted into the body wall 41, one end part (outside the body) functions as a stopper. Accordingly, the camera support tube 13 does not fall out to the inside of the body, and it is possible to fix the cannula 31 to the body wall 41.

In addition, inside one end part (outside the body), a structure in which a valve 37 having restoration properties is provided. The valve 37 has a valve structure which is pressingly expanded to the center part thereof when an external force is applied toward the narrow end part (inside the body) from the thick end part (outside the body).

In addition, it is preferable that the cannula 31 has a small diameter for realizing low invasiveness. Specifically, it is preferable that the diameter of the cannula 31 is equal to or smaller than 3 mm.

In a case where the camera unit 11 is joined to the camera support tube 13 in the body, first, as illustrated in FIG. 4(b), in a state where the camera side cable 12 passes through inside the camera support tube 13, the camera support tube 13 is inserted into the cannula 31 until the narrow end part of the camera support tube 13 is pushed against the thick (outside the body) end part of the cannula 31, and the narrow end part of the camera support tube 13 is exposed from the cannula 31. At this time, the valve 37 is pressingly expanded by the camera support tube 13, the camera support tube 13 is tightly fastened by a biasing force caused by restoration properties, and as a result, the camera support tube 13 is fixed to the cannula 31. In addition, the thick end part (outside the body) of the camera support tube 13 is also exposed from the cannula 31.

Next, as illustrated in FIG. 4(c), by inserting the narrow tip part (inside the body) of the camera support tube 13 into the recessed support tube joining portion 14 by using the camera side cable 12 as a guide, the locking claw 23 is fitted to the locking hole 123, and the camera unit 11 and the camera support tube 13 join with each other with high mechanical strength. In addition, if the locking claw 23 and the locking hole 123 join each other, any shape may be employed, and O ring or the like can be used instead of the locking claw 23.

In addition, it is desirable that strength by which the camera support tube 13 and the support tube joining portion 14 are fitted to each other is set to be smaller than adhering strength of an adhesion and fixing unit which adheres and fixes the camera side cable 12 and the camera unit 11 to each other. This is because there is a concern that the adhering and fixing unit is destroyed and the body wall of a patient is damaged as the camera unit is pulled outward of the body, if the fitting strength (joining strength) of the camera support tube 13 and the support tube joining portion 14 is greater than the adhering strength of the adhering and fixing unit, since it is necessary to insert the camera support tube 13 while holding, pulling, and supporting the cable, and using the cable as a guide, when inserting the camera support tube 13 into the support tube joining portion 14 of the camera unit 11.

Specifically, it is desirable that the strength by which the camera support tube 13 and the support tube joining portion 14 are fitted to each other is equal to or less than 30 N (newton) which is smaller than the adhering strength of the adhesion and fixing unit. Furthermore, it is desirable that the most appropriate range is set to be a range of 3 N to 6 N. If the range is set, a special effect is achieved in which the camera support tube 13 and the support tube joining portion 14 can be fitted to each other without applying an excessively large force during the fitting, and installation can be safely performed without continually applying the excessive force since the feeling that the camera support tube 13 is fitted is transferred to the hand.

Figure 13:
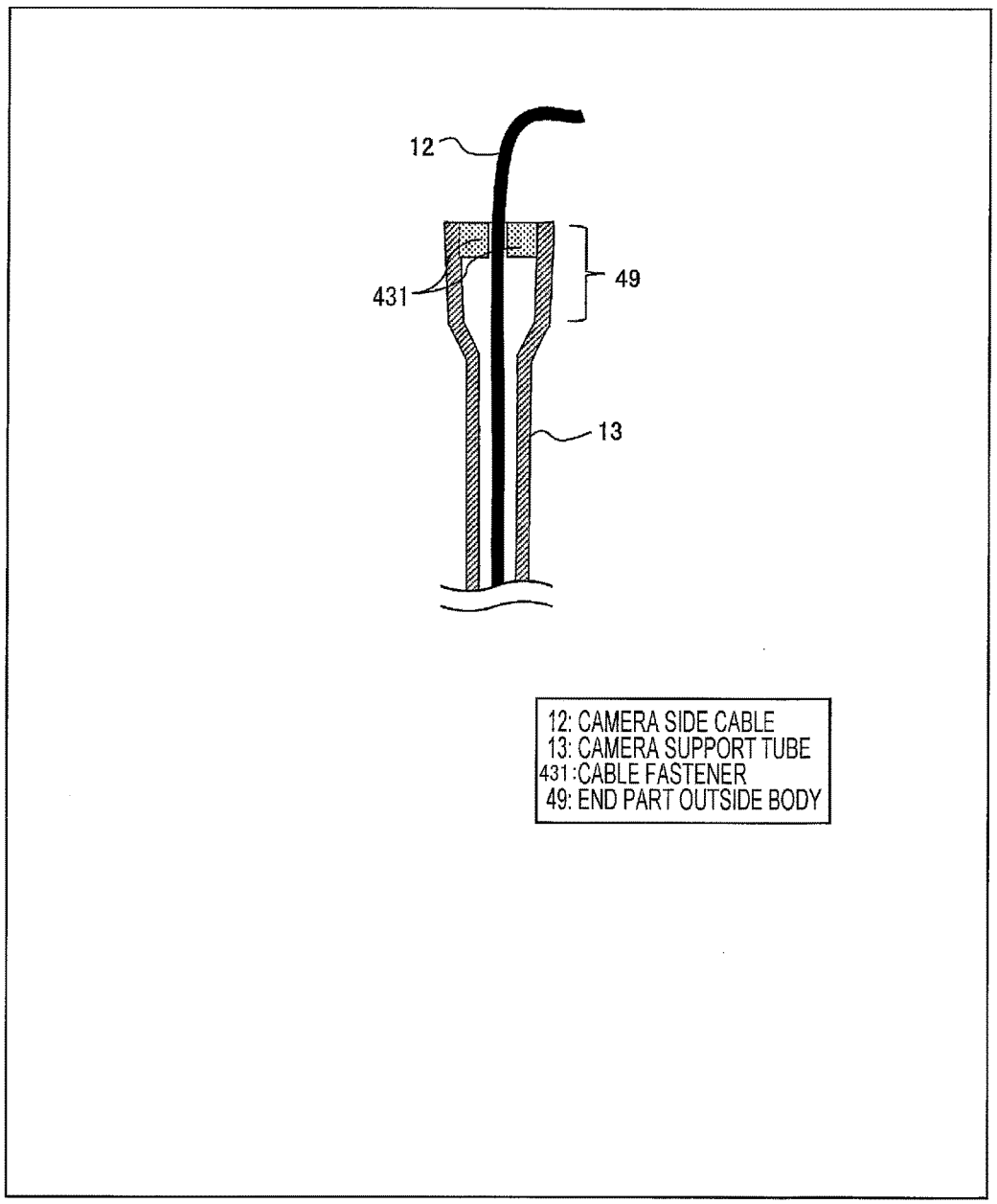
FIG. 13 is a sectional view illustrating a configuration example of a cable fastener.

In addition, above, it is described that the tip end of the camera support tube 13 is a sharpened or is diagonally cut in a round shape similar to a needle, and may also be used as a puncturing device. However, a configuration in which the camera support tube 13 and the camera unit 11 are indirectly fixed to each other by making a shape only for the insertion into the support tube joining portion 14 without the fitting by the locking claw or the like is provided, and by fixing the camera side cable 12 to the camera support tube 13 by the cable fastener 431 (cable holder) provided at an end part outside of the body 49 of the camera support tube 13 as illustrated in FIG. 13, may be employed. In addition, the cable fastener 431 may be the same body or may be separated bodies from the camera support tube 13.

Here, in order to prevent the camera support tube 13 from being removed from the support tube joining portion 14 provided in the camera unit 11, it is necessary to increase the cable holding strength of the cable fastener 431 which holds the camera side cable 12 in the camera support tube 13, to be greater than the joining strength of the camera support tube 13 and the camera unit 11. Specifically, for example, in a case where the fitting strength of the inserted camera support tube 13 is within a range of 3 N to 6 N, strength which is greater than the range, that is, strength which is equal to or greater than at least 5 N, is necessary. In addition, since it is not necessary that the fitting strength is equal to or greater than the strength of the cable, it is desirable that the most appropriate range is from 5 N to 50 N.

According to the above-described holding strength, since the camera support tube 13 and the support tube joining portion 14 sufficiently come into contact with each other, when the side surfaces of the camera support tube 13 and the support tube joining portion 14 are formed of a material having high thermal conductive properties, it is possible to improve heat radiation properties of the camera unit 11.

Figure 12:
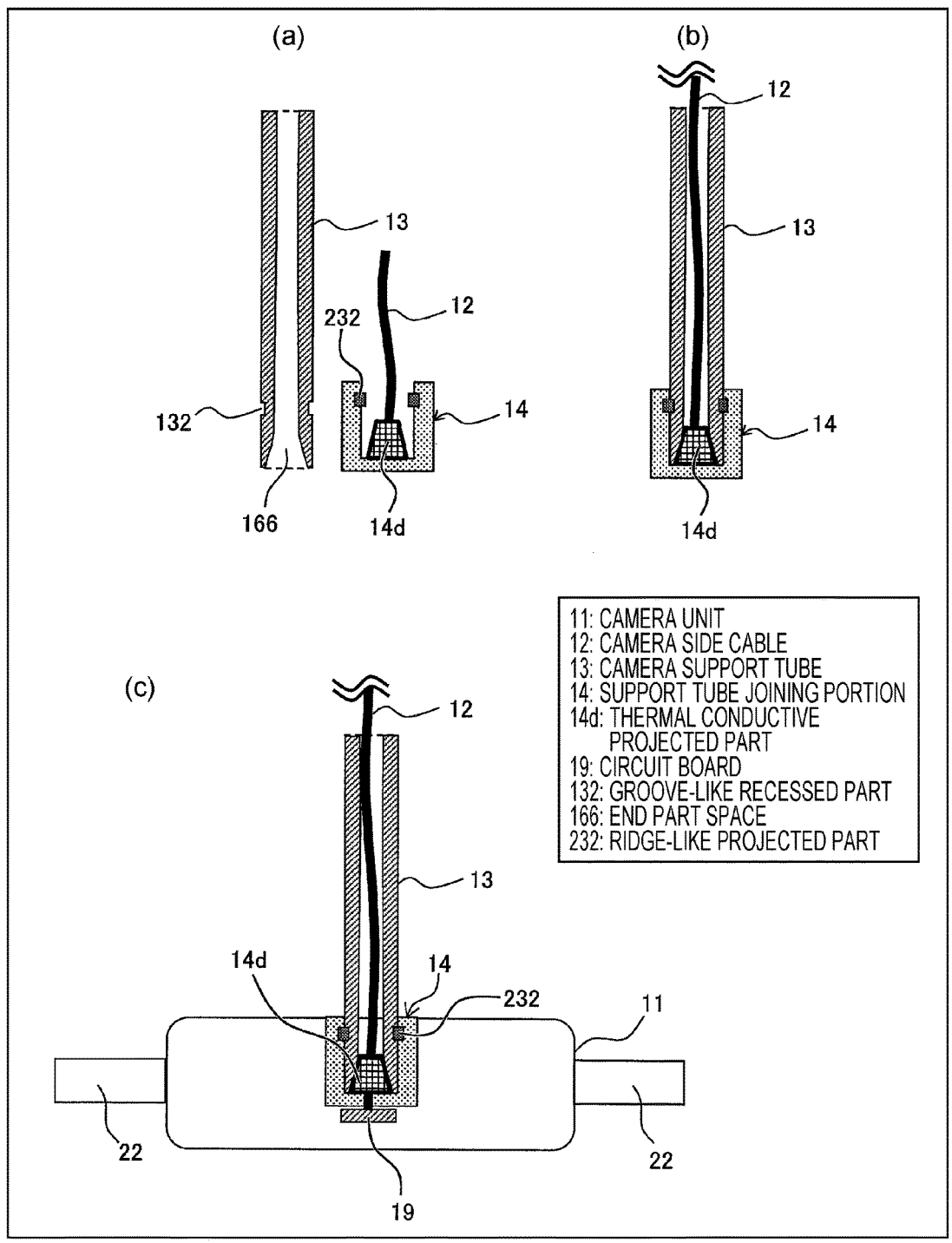
FIG. 12 is a sectional view illustrating another configuration example of the camera support tube and the support tube joining portion.

FIG. 12 illustrates an example of a configuration in which the above-described joining properties or heat radiation properties is improved. FIG. 12(a) is a sectional view of the camera support tube 13 and the support tube joining portion 14. FIG. 12(b) is a sectional view illustrating a state where the camera support tube 13 is inserted into the support tube joining portion 14. FIG. 12(c) is a sectional view illustrating a joined state of the camera support tube 13 and the camera unit 11 illustrated in FIG. 2.

As illustrated in FIGS. 12(a) and 12(b), the groove-like recessed part 132 which goes round the outer side surface is provided at the end part inside the body of the camera support tube 13, the ridge-like projected part 232 which goes round the inner side surface is provided in the opposing support tube joining portion 14.

Furthermore, the support tube joining portion 14 has a thermal conductive projected part 14d which is made of a metal material having excellent thermal conductive properties at the bottom part, and the camera side cable 12 is adhered and fixed to the inside of the thermal conductive projected part 14d. In this case, the camera side cable 12 is drawn out from the thermal conductive projected part 14d of the support tube joining portion 14. An example of the adhesion and fixing includes sealing and fixing by compression, an adhesive, or an O ring. Accordingly, intrusion of water and mixing of foreign materials into the camera unit 11 from the adhered and fixed part, are prevented.

More specifically, the thermal conductive projected part 14d has a shape of a tapered truncated cone when approaching an opening unit of the support tube joining portion 14, the camera side cable 12 passes through a hole formed in an axial direction, and the camera side cable 12 and the thermal conductive projected part 14d are adhered and fixed in the hole. The inside (end part space 166) of the end part (inside the body) of the camera support tube 13 joined to the support tube joining portion 14 has a reversed tapered shape (shape of which the inner diameter increases when approaching the tip end) which corresponds to the shape of a truncated cone of the thermal conductive projected part 14d. Accordingly, when joining the camera support tube 13 by using the camera side cable 12 as a guide, since the reversed tapered end part space 166 of the camera support tube 13 is guided to the thermal conductive projected part 14d of the support tube joining portion 14, insertion of the camera support tube 13 becomes easy.

In addition, when the camera support tube 13 is fitted into the support tube joining portion 14, since an outer circumferential surface of the end part of the camera support tube 13 comes into contact with an inner side wall of the support tube joining portion 14, and an inner circumferential surface of the end part of the camera support tube 13 comes into contact with the thermal conductive projected part 14d of the support tube joining portion 14, a special effect is achieved in which joining properties of the camera support tube 13 and the support tube joining portion 14 increases, and heat radiation properties of the heat transferred to the camera support tube 13 from the camera unit 11 is further improved.

In a case where the end part space 166 of the camera support tube 13 has a reversed tapered shape, it is desirable that the outer diameter of the camera support tube 13 does not become thicker by making the outer diameter of the camera support tube 13 constant or by making the camera support tube 13 in a slightly tapered shape to be thinner toward the tip end. In this manner, when the camera support tube 13 is inserted into the tube-like device, such as a cannula, it is possible to avoid a situation in which the camera support tube 13 is hooked to the inner wall of the tube-like device and the camera support tube 13 does not fall out.

(Method of Use and Effect of In-vivo Monitoring Camera System 1 in Embodiment 1)

Figure 6:
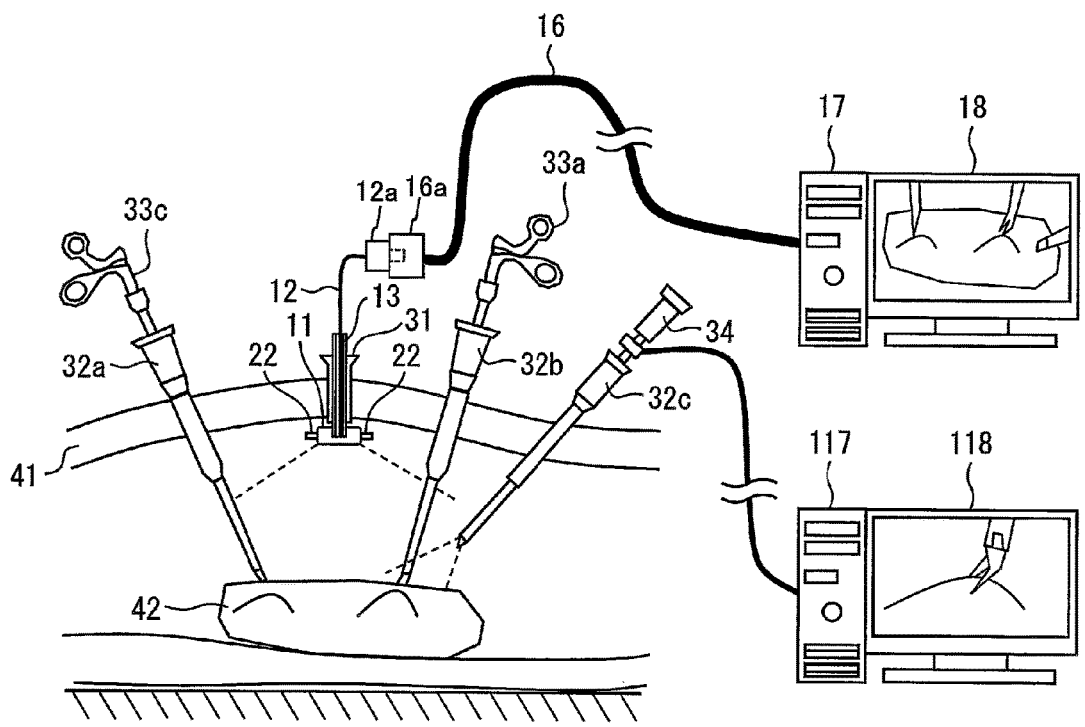
FIG. 6 is a schematic view illustrating a method of use of the camera unit according to Embodiment 1.

FIGS. 5(a) to 5(g) are schematic views illustrating a method for installing the camera unit 11 according to Embodiment 1 in the body. FIG. 6 is a schematic view illustrating a situation of use of the in-vivo monitoring camera system 1 according to Embodiment 1.

As illustrated in FIG. 5(a), first, a practitioner opens a hole (port) on the abdominal wall 41 for inserting forceps or an endoscope into the body cavity, and inserts trocars 32a to 32c into the port. Furthermore, in order to install the camera unit 11 in the body cavity, the port is opened at a position where the entire organ including the affected part can be seen on the abdominal wall 41, and the cannula 31 is inserted. Specifically, in a state where a needle-like obturator passes through the inside of the cannula 31, the obturator is punctured through the port, and accordingly, the cannula 31 is inserted into the abdominal wall 41. In addition, it is preferable that the diameter of the cannula 31 is short for realizing low invasiveness. Specifically, it is preferable that the diameter of the cannula 31 is equal to or less than 3 mm. In addition, after at least one of the trocars 32a to 32c and cannula 31 is inserted, the practitioner sends gas into the body through the trocars 32a to 32c, inflates the inside of the body cavity in advance, and ensures a space into which the instrument is inserted.

Next, as illustrated in FIG. 5(b), the practitioner inserts an endoscope 34 through the trocar 32c into the body cavity, and inserts the camera unit 11 gripped by forceps 33a into the body cavity through the trocar 32b while observing the inside of the body by using the endoscope 34.

Next, as illustrated in FIG. 5(c), the practitioner operates the forceps 33a, moves the camera unit 11 to be close to the cannula 31, and inserts forceps 33b into the body cavity through the cannula 31.

Next, as illustrated in FIG. 5(d), the practitioner leads the camera side cable 12 to the outside of the body by pulling out the forceps 33b from the cannula 31 in a state of nipping the camera side cable 12 by the forceps 33b. At this time, the camera unit 11 (gripping portion 22 thereof) becomes gripped by the forceps 33a.

Next, as illustrated in FIG. 5(e), the practitioner inserts the forceps 33c through the trocar 32a, and while gripping the gripping portion 22 on both side surfaces of the camera unit 11 by the two forceps 33a and 33c, the practitioner makes the camera side cable 12 guided toward the outside of the body pass through the inside of the camera support tube 13, and inserts the camera support tube 13 into the cannula 31 so that the support tube joining portion 14 of the camera unit 11 and the opening of the cannula 31 become parallel and close to each other.

Next, as illustrated in FIG. 5(f), the practitioner inserts the end part of the camera support tube 13 exposed from the cannula 31 into the support tube joining portion 14 (FIG. 1) of the camera unit 11 by using the camera side cable 12 as a guide, and joins the camera support tube 13 and the camera unit 11 to each other.

In addition, when the camera support tube 13 is inserted into the support tube joining portion 14 of the camera unit 11, a force (for example, 3 N to 6 N) necessary for fitting the camera support tube 13 and the support tube joining portion 14 to each other, is sufficiently reduced to be smaller than the adhering strength (for example, equal to or greater than 30 N) of the adhering and fixing unit of the camera side cable 12 and the camera unit 11 when the camera support tube 13 is inserted into the support tube joining portion 14 of the camera unit 11. Therefore, by pulling the cable while using the cable as the guide, it is possible to safely insert the camera support tube 13, and make the camera support tube 13 fitted.

Next, as illustrated in FIG. 5(g), the practitioner pulls up the camera support tube 13 and brings the camera unit 11 into contact with the end part inside the body of the cannula 31, so that the widest area possible inside of the body cavity can be imaged. Since the camera support tube 13 is tightly fastened by the valve 37 (refer to FIG. 4) of the cannula 31, the camera support tube 13 and the camera unit 11 maintain the fastened state.

As illustrated in FIG. 6, after installing the camera unit 11 in the body, the camera side cable 12 and the instrument side cable 16 are joined to each other by using the connectors 12a and 16a. Accordingly, a local image of a treatment part is displayed on a display 118 by an endoscope control instrument 117, and the entire image of an organ 42 imaged by the camera unit 11 is displayed on the display 18 by the camera unit control instrument 17.

Figure 11:
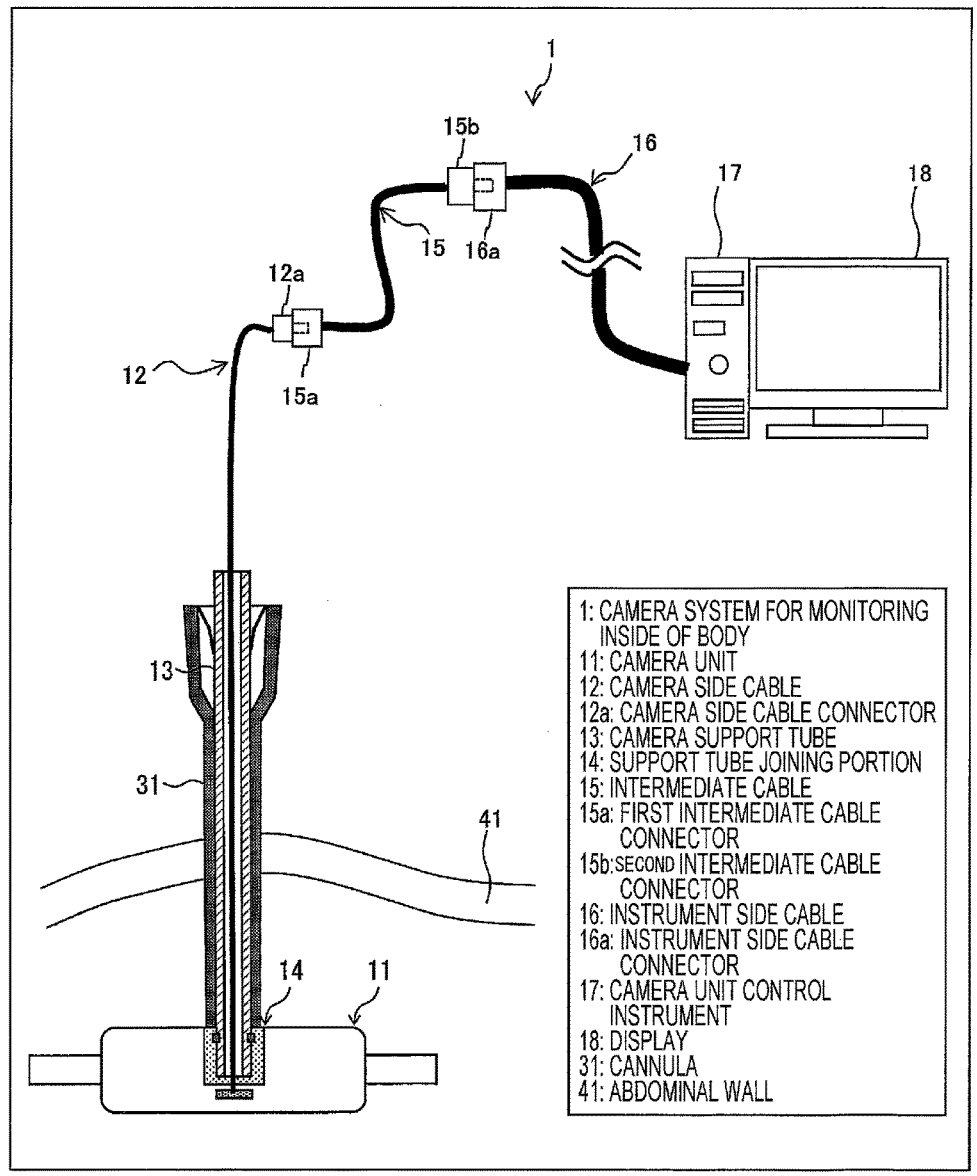
FIG. 11 is a schematic view illustrating another configuration of the in-vivo monitoring camera system according to Embodiment 1.

In addition, as illustrated in FIG. 11, it is desirable that an intermediate cable 15 is provided between the camera side cable 12 and the instrument side cable 16. In this manner, since it is possible to gradually convert the diameter of the extremely thin camera side cable 12 and the thick instrument side cable 16 or the thickness of the cable connector, and to use the extremely thin cable having a relatively low transfer speed as a minimum necessary speed, it is possible to increase the transfer speed to be high, and to obtain a high resolution image. In this case, as a camera side cable connector 15a and a first intermediate cable connector 15a of the intermediate cable 15 are fitted to each other, the camera side cable 12 and the intermediate cable 15 are connected to each other. In addition, as the instrument side cable connector 16a and a second intermediate cable connector 15b of the intermediate cable 15 are fitted to each other, the instrument side cable 16 and the intermediate cable 15 are connected to each other. In this example, in a case where the cable diameter or the thickness of the cable connector are gradually converted, "the outer diameter of the camera side cable 12<the outer diameter of the intermediate cable 15<the outer diameter of the instrument side cable 16" and "the outer diameter of the camera side cable connector 12a≤the outer diameter of the first intermediate cable connector 15a<the outer diameter of the second intermediate cable connector 15b≤the outer diameter of the instrument side cable connector 16a", are desirable.

In addition, by using the intermediate cable 15, a special effect is achieved in which a clean field and an unclean field are effectively separated during the surgery. In other words, in order to improve the above-described transfer speed or easier handling during the installation, the camera side cable 12 which is put into the body is set to have a minimum necessary length, and the intermediate cable 15 which has already been sterilized is used until the cable exceeds the clean field and enters the unclean field. In this manner, it is possible to fit the camera side cable connector 12a of the camera side cable 12 and the first intermediate cable connector 15a to each other in the clean field, and to maintain the clean state. Meanwhile, the second intermediate cable connector 15b is fitted to the instrument side cable connector 16a of the instrument side cable 16 which is in the unclean field, becomes unclean, and is handled as an unclean instrument after the fitting. Therefore, it is possible to completely separate the unclean instrument from the clean instrument side.

In addition, at a part included in the "clean field" in the in-vivo monitoring camera system, sterilization treatment is performed and cleanness is maintained. Meanwhile, a part included in the "unclean field" is a part at which the sterilization treatment is not performed, or a part which entered the unclean field after the sterilization treatment is performed.

In addition, it is desirable that connecting strength (fitting strength) when the camera side cable 12, the intermediate cable 15 or the instrument side cable 16 are connected (fitted) to each other by the connectors 12a and 15a or by the connectors 12a and 16a, is set to be smaller than the adhering strength of the adhering and fixing unit which adheres and fixes the camera side cable 12 and the camera unit 11.

This is for eliminating a concern that the adhering and fixing unit of the camera side cable 12 is destroyed or a body wall of the patient is damaged by pulling the camera unit 11 in the outward direction of the body as the connected (fitted) part by the connectors 12a and 15a or by the connectors 12a and 16a previously, when an unexpected large force is applied to the cable during the normal use, and for improving safety. In addition, it is possible to prevent an accident that the practitioner or an assistant hooks the cable and falls, or the camera unit control instrument 17 is pulled from the table and drops.

For example, specifically, it is desirable that the strength by which the cables are connected (fitted) to each other by the connectors 12a and 15a or by the connectors 12a and 16a is equal to or less than 30 N (newton) which is smaller than the adhering strength of the adhering and fixing unit. Furthermore, it is desirable that the most appropriate range is set to be a range of 4 N to 10 N. If the range is set, it is possible to connect the cables without applying an excessively large force during the connecting, and it is also not necessary to apply an excessively large force during removing.

In addition, when the fitting strength of the instrument side cable connector 16a and the second intermediate cable connector 15b which are in the unclean field, or the fitting strength of the instrument side cable 16 and the camera unit control instrument 17 by a cable connector (not illustrated) which is on the camera unit control instrument 17 side in the instrument side cable 16, is set to be greater than the fitting strength of the camera side cable connector 12a and the first intermediate cable connector 15a (for example, 50 N to 100 N), when an unexpected force is applied to the cable, the connection (the fitting of the camera side cable connector 12a and the first intermediate cable connector 15a) of the camera side cable 12 and the intermediate cable 15 in the clean field can be set to be released in advance.

In reverse, for example, if the connection (the fitting of the instrument side cable 16a and the second intermediate cable connector 15b) of the intermediate cable 15 and the instrument side cable 16 in the unclean field is released in advance, a risk that a part in the unclean field of the intermediate cable and the second intermediate cable connector enter the cleaned field in reaction, is generated. Therefore, a special effect is achieved in which the release of the connection in the clean field in advance ensures safety during the surgery.

In addition, in a case where the connection is released in the clean field, and a part of the intermediate cable in the clean field, that is, a part (clean part) having a predetermined length from the fitted part of the camera side cable connector 12a and the first intermediate cable connector 15a in the intermediate cable 15, and the first intermediate cable connector 15a, comes into contact with the unclean field, the part may be exchanged with the clean intermediate cable 15 (including the first intermediate cable connector 15a), and thus, safety is achieved. In addition, in a case where the connector is an independent component, and in a case where the connector comes into contact with both the clean field and the unclean field of the intermediate cable 15, the intermediate cable 15 and the connector may be exchanged with the clean intermediate cable 15 and the clean connector.

In addition, it is desirable that the camera side cable 12 is sufficiently short compared to the length (1 m) added by the camera side cable 12 and the clean part. Specifically, it is desirable that the camera side cable 12 is equal to or shorter than a half of the length added by the camera side cable 12 and the clean part, that is, maximum 50 cm. Accordingly, it is possible to prevent the camera side cable 12 from entering the unclean field. In addition, it is desirable that the camera side cable 12 is shorter than the sum of the length of the camera support tube 13 and the length of the cannula 31 (tube-like device) which passes through the camera support tube 13.

In the above-described example, a case where the camera side cable 12 and the instrument side cable 16 are connected by the intermediate cable 15 is described, but in a case where the camera side cable 12 and the instrument side cable 16 are directly connected to each other, it is also desirable that the camera side cable 12 is sufficiently short compared to the length (approximately 1 m) added by the camera side cable 12 and the clean part. In this case, the clean part is a part having a predetermined length from the fitted part of the camera side cable connector 12a and the instrument side cable connector 16a in the instrument side cable 16.

Accordingly, the practitioner can perform treatment by the forceps 33a and the forceps 33c while enlarging and observing the work region (local region) on the display 118, and can ascertain the state (movement of the forceps or the like, a bleeding site, and a residual, such as gauze, outside the work region) outside the work region on the display 18.

In addition, the camera unit 11 and the camera support tube 13 join with each other with high mechanical strength, and the supporting force of the camera unit 11 is higher than that in the related art. In addition, since the camera side cable 12 is guided toward the outside of the body through the inside of the camera support tube 13, after the camera unit 11 and the camera support tube 13 join each other, a load is not applied to the camera side cable 12, the camera side cable 12 is not exposed to the inside of the body, and the camera side cable 12 does not come into contact with the abdominal wall 41. Accordingly, certainty (waterproof and stainproof properties of the connected part) of the electric connection of the camera side cable 12 and the circuit board 19 (FIG. 2) is increased. Therefore, it is possible to realize the in-vivo monitoring camera system 1 having high reliability.

In addition, the practitioner can operate the camera support tube 13 according to the situation, and can change an orientation (direction of the visual field) of the camera unit 11. Specifically, by using elasticity of the abdominal wall 41, the practitioner can change the orientation of the camera unit 11 by inclining the camera support tube 13. At this time, when the practitioner takes off the hand from the camera support tube 13, the orientation returns to the original orientation due to elasticity of the abdominal wall 41, and thus, it is possible to improve efficiency of work of the practitioner. In addition, since both the cannula 31 and the camera support tube 13 inserted into the cannula 31 are cylindrical tubes, it is possible to easily rotate the camera support tube 13 in the circumferential direction. Accordingly, the practitioner can change the orientation of the camera unit 11 without applying a load to the abdominal wall 41. In addition, since the camera support tube 13 is held to be movable in the longitudinal direction (extending direction of the tube) by the cannula 31, the practitioner can change imaging zoom without applying a load to the abdominal wall 41 by pushing the camera support tube 13 to the inside of the body, and by pulling up the camera support tube 13 to the outside of the body. Accordingly, it is possible to realize the in-vivo monitoring camera system 1 having high usability.

The cannula 31 and the camera support tube 13 are fixed to each other by the valve 37 in the cannula 31 in Embodiment 1, but in a case where a general cannula which is not provided with the valve 37 is used, it is possible to fix the cannula 31 and the camera support tube 13 by a tape.

(Separation of Camera Unit 11 and Camera Support Tube 13)

Next, a method for separating the camera unit 11 and the camera support tube 13 will be described. First, the practitioner pulls the camera support tube 13 in the outward direction of the body in a state where the gripping portion 22 of the camera unit 11 is gripped by the forceps 33a and the forceps 33c, and pulls out the camera support tube 13 from the support tube joining portion 14 of the camera unit 11. Next, the practitioner leads the camera unit 11 and the camera side cable 12 to the outside of the body from the trocar 32a or the trocar 32b after pulling out the camera support tube 13 from the cannula 31 and separating the camera support tube 13 and the camera side cable 12 from each other. Otherwise, the camera support tube 13 may be pulled out from the hole which is opened for pulling out a respected organ.

Similar to the time when the camera unit 11 and the camera support tube 13 are separated from each other, it is desirable that the fitting strength of the camera support tube 13 and the support tube joining portion 14 is set to be smaller than the adhering strength of the adhering and fixing unit which adheres and fixes the camera side cable 12 and the camera unit 11. This is because there is a concern that the adhering and fixing unit is destroyed and the body wall of the patient is damaged as the camera unit is pulled in the outward direction in relation to the body, since it is necessary to apply a large force when removing the camera support tube 13 from the camera unit 11 if the fitting strength (joining strength) of the camera support tube 13 and the support tube joining portion 14 is greater than the adhering strength of the adhering and fixing unit.

For example, if the fitting strength is set to be in a range of 3 N to 6 N, a special effect is achieved in which the camera support tube 13 can be removed without applying an excessively large force, and the camera support tube 13 can be safely separated without continually applying the excessive force since the feeling that the camera support tube 13 is removed is transferred to the hand.

In addition, the camera side cable connector 12a passes through the inside of the body during the withdrawing, but as described above, there is not a problem in maintaining cleanness.

(Heat Radiation Means Inside Camera Unit 11)

Next, heat radiation of the camera unit 11 (in-vivo monitoring camera) which is fixed to the abdominal wall 41, will be described. The heat generated in each component provided in the above-described camera unit 11 in FIG. 2, is conducted as follows.

First, the heat generated in the solid-state imaging device 25 is transferred to the circuit board 19 via a terminal of the solid-state imaging device 25. In addition, the heat transferred to the circuit board 19 is transferred to the support tube joining portion 14 which is in contact with the circuit board 19. Otherwise, the heat transferred to the circuit board 19 is transferred to the support tube joining portion 14 separated from the circuit board 19. Similar to the heat generated in the illumination apparatus 27, the heat is transferred to the support tube joining portion 14 via the circuit board 19.

As illustrated in FIG. 4(c), the support tube joining portion 14 and the circuit board 19 are disposed to oppose each other through a surface. Therefore, the heat generated in the camera unit 11 is conducted to the support tube joining portion 14 via the circuit board 19. In addition, the heat is discharged from the camera unit 11 through the camera support tube 13. It is preferable that the circuit board 19 and the support tube joining portion 14 are thermally connected to each other by an adhesive or grease which has high thermal conductivity. In this case, the adhesive or grease which has high thermal conductivity functions as a thermal conductor for transferring the heat generated in the solid-state imaging device 25 and the illumination apparatus 27 to the support tube joining portion 14 via the circuit board 19.

Figure 7:
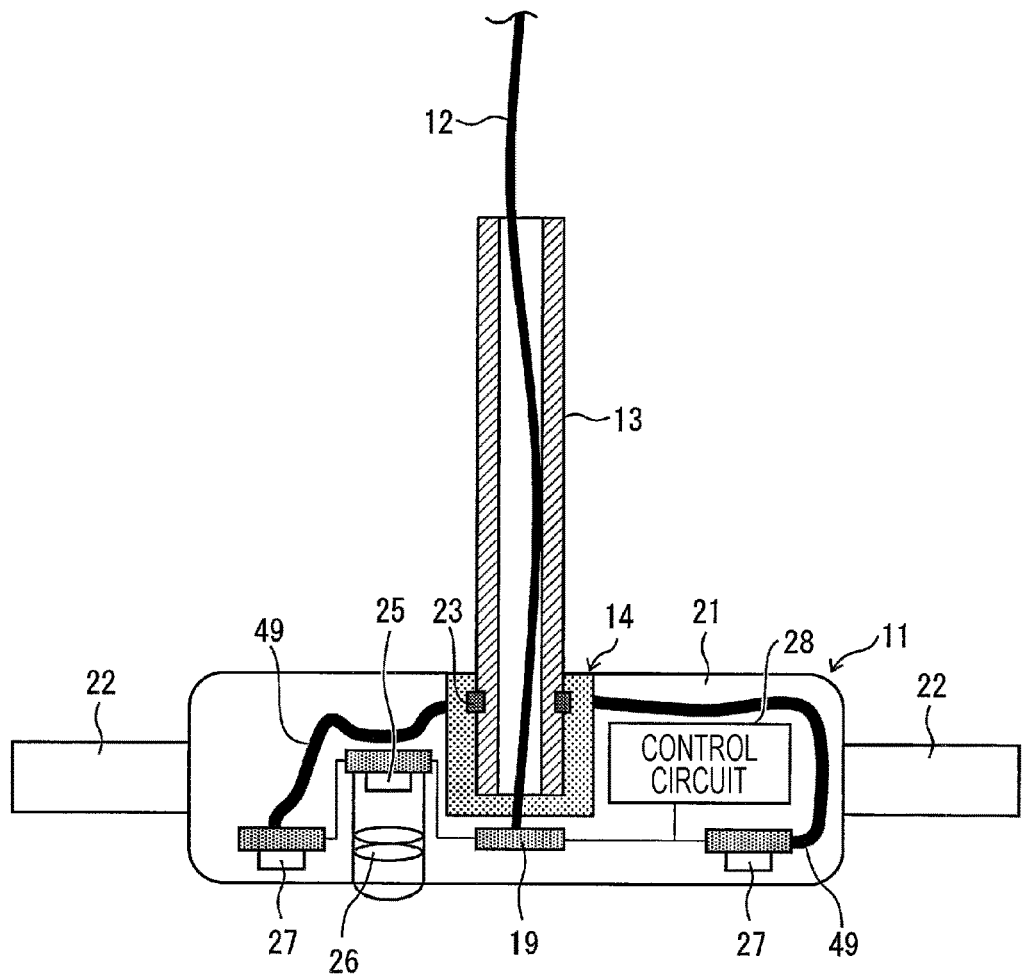
FIG. 7 is a schematic sectional view of a camera unit and a camera support tube according to Embodiment 2.

FIG. 7 is a schematic sectional view of the camera unit 11 and the camera support tube 13 according to Embodiment 2. It is preferable that the illumination apparatus 27, the solid-state imaging device 25, and the control circuit 28, which are heat sources are thermally connected to the camera support tube 13 via the support tube joining portion 14 by a thermal conductor 49 having high thermal conductivity. Accordingly, it is possible to directly transfer the heat generated from the illumination apparatus 27, the solid-state imaging device 25, and the control circuit 28, to the support tube joining portion 14 without going through the circuit board 19. As a result, it is possible to more efficiently discharge the heat generated in the camera unit 11. As the thermal conductor 49, a silicon rubber having heat radiation properties can be used, but the thermal conductor 49 is not limited thereto.

Thermal resistance between the illumination apparatus 27, the solid-state imaging device 25, and the control circuit 28, which are the heat sources, and the camera support tube 13, depends on an amount of generated heat of the heat source, but is preferably equal to or less than 20° C./W.

In a case where there is a possibility that an outer surface of the camera unit 11 comes into contact with the abdominal wall 41, it is necessary to set the temperature of the outer surface to be equal to or lower than 41° C. In order to emit the heat generated from the camera unit 11 to the outside of the body, it is desirable that the thermal resistance from a heat generating unit of the camera unit 11 to the support tube joining portion 14 is equal to or less than 20° C./W when the room temperature is 25° C., the difference of the temperature is 16° C., and the amount of generated heat of the camera unit 11 is 0.75 W.

The camera housing 21 can come into contact with the abdominal wall 41. Therefore, it is necessary to make it difficult to transfer the heat inside the camera unit 11 to the abdominal wall 41 through the camera housing 21. Therefore, it is desirable that the thermal conductivity (housing thermal conductivity) of the camera housing 21 is lower than the thermal conductivity (support tube thermal conductivity) of the camera support tube 13.

When the thermal conductivity of the camera support tube 13 is higher than the thermal conductivity of the camera housing 21, since the heat is transferred to the camera support tube 13 prior to the camera housing 21 and the heat radiation from the camera support tube 13 is performed, it is possible to prevent the heat of the camera housing 21 from ascending.

(Material of Camera Unit 11)

It is appropriate that the camera housing 21 is configured of a resin, such as polycarbonate. The thermal conductivity of the resin is approximately 0.2 W/(m·K). However, the material of the camera housing 21 is not limited thereto.

In order to efficiently discharge the heat generated in the camera unit 11 through the camera support tube 13, it is preferable that the material of the camera support tube 13 and the support tube joining portion 14 is a material having high thermal conductivity. Examples of the material include Ag, Cu, Al, SUS, brass, and a ceramic-based material. However, the material of the camera support tube 13 and the support tube joining portion 14 is not limited to the above-described materials.

It is necessary to set the thermal conductivity of the camera support tube 13 and the support tube joining portion 14 to be higher than the thermal conductivity of the camera housing 21 as described above. It is desirable that the thermal conductivity is the thermal conductivity (high thermal conductivity) which is equal to or greater than 1.0 W/(m·K), that is, at least 5 times 0.2 W/(m·K) which is the thermal conductivity of the resin that configures the camera housing 21.

[Embodiment 2]

The camera support tube 13 and the support tube joining portion 14 may be respectively configured of a plurality of materials. In Embodiment 1, the locking hole (recessed part) is provided on the side surface of the camera support tube, and the locking claw (projected part) is provided on the side surface of the support tube joining portion. However, at least one of the support tube recessed part and the joining portion projected part may be configured of a material having elasticity, such as a resin, and the other one may be configured of a hard material, such as metal. For example, the locking claw 23 or the locking claw 523 may be configured of a material having elasticity, such as a resin.

In this configuration, during the joining, the elastic material is transformed and passes through a location at which the locking claw 23 (elastic material) of the joining portion is disposed and which is slightly narrow, returns to an original shape by an elastic force after passing through the location, and is firmly fitted. Therefore, the joining strength is improved. The invention is not limited to the example, and at least one of the recessed and projected part of the support tube and the joining portion may be formed of the elastic material.

In this manner, since the feeling of fitting is transferred to the hand, the practitioner who performs the operation feels the response of the fitting, and can recognize that the fitting is performed. Therefore, it is also advantageous that it is not necessary to continue to apply an excessive force.

Therefore, the heat radiation properties from the camera unit is improved by forming the support tube and the side surface of the joining portion by the material having high thermal conductive properties, the joining strength is improved by using the elastic material only in the projected part of the joining portion, and the function of feeing the response of the fitting is added. According to this, if a plurality of materials having different characteristics from each other is used, it is possible to establish a plurality of required performance including the joining properties and the heat radiation properties.

Regardless of the above-described configuration example, the materials may be combined in reverse. In other words, the locking claw may be configured of the hard material, such as metal, and the part including the locking hole may be configured of the material having elasticity, such as a resin.

Various examples are described above, but it is needless to say that the configuration materials of the support tube and the joining portion may be similarly combined in plural manners in other embodiments.

[Embodiment 3]

Figure 8:
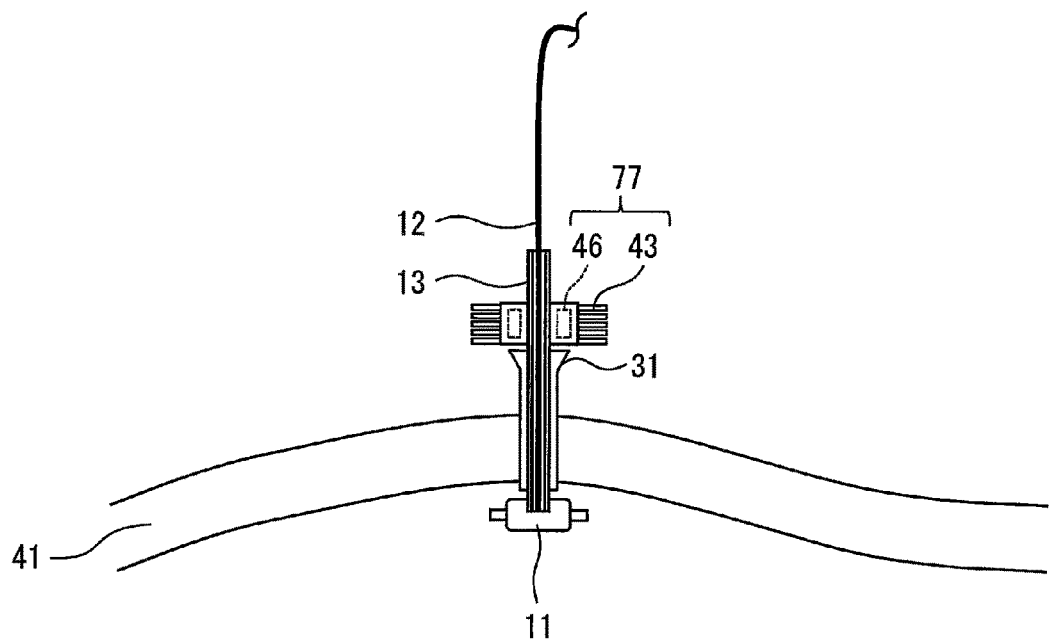
FIG. 8 is a schematic sectional view of a camera unit and a camera support tube according to Embodiment 3.

FIG. 8 is a schematic sectional view of the camera unit 11 and the camera support tube 13 according to Embodiment 3. A heat sink 43 (heat discharging unit of an in-vivo monitoring camera, heat radiation amount increasing unit) is provided at a location which is exposed to the outside of the body from the cannula 31 of the camera support tube 13. The heat sink 43 disperses the heat which is generated from the camera unit 11 and conducted to the camera support tube 13.

The heat sink 43 may be integrally molded with the camera support tube 13, but may be attached to the camera support tube 13 after combining the camera support tube 13 to the camera unit 11. It is preferable that the heat sink 43 is also configured of a material which has higher thermal conductivity than that of the camera housing 21, similar to the camera support tube 13.

By attaching the heat sink 43 to the camera support tube 13, a surface area which discharges the heat from the camera support tube 13 increases. Therefore, the discharge amount of the heat from the camera support tube 13 to the air increases. As a result, the efficiency of the heat radiation of the camera unit 11 is improved.

In order to further increase the discharge amount of the heat from the camera support tube 13 to the air, it is preferable to provide a heat radiation fan 46 for increasing the movement amount of the air which is in contact with the heat sink 43. The heat radiation fan 46 sends the wind to the heat sink 43, or discharges the air in the vicinity of the heat sink 43. In this manner, in FIG. 8, a cooling system 77 is configured to include the heat sink 43 (heat radiating unit) which discharges the heat transferred from the camera support tube 13 to the air, and the heat radiation fan 46 (heat radiation amount accelerating unit) which sends the wind to the heat sink 43.

[Embodiment 4]

Figure 9:
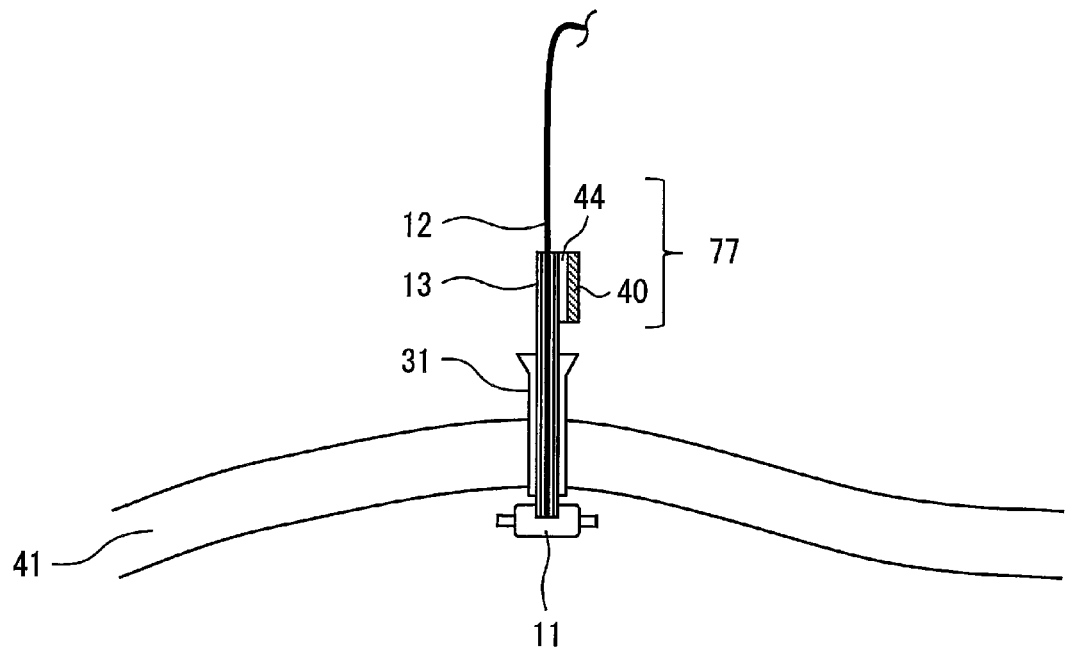
FIG. 9 is a schematic sectional view of a camera unit and a camera support tube according to Embodiment 4.

FIG. 9 is a schematic sectional view of the camera unit 11 and the camera support tube 13 according to Embodiment 4. A low temperature material attaching plate 44 is attached to be in contact with a wide area at a location which is exposed to the outside of the body from the cannula 31 of the camera support tube 13. In addition, a low temperature material 40 (heat discharging unit of an in-vivo monitoring camera, conducted heat absorbing unit) is provided on the low temperature material attaching plate 44. The low temperature material 40 absorbs the heat which is generated from the camera unit 11 and conducted to the camera support tube 13 via the low temperature material attaching plate 44. In this manner, in FIG. 9, the cooling system 77 is configured to include the low temperature material attaching plate (cooling material attaching plate) 44, and the low temperature material 40 (cooling material, heat absorbing unit) which absorbs the heat transferred via the low temperature material attaching plate 44 from the camera support tube 13.

As the low temperature material 40, a case in which a frozen cold insulating material and dry ice are input, can be used. However, the material is not limited thereto if the material absorbs the heat.

[Embodiment 5]

Figure 10:
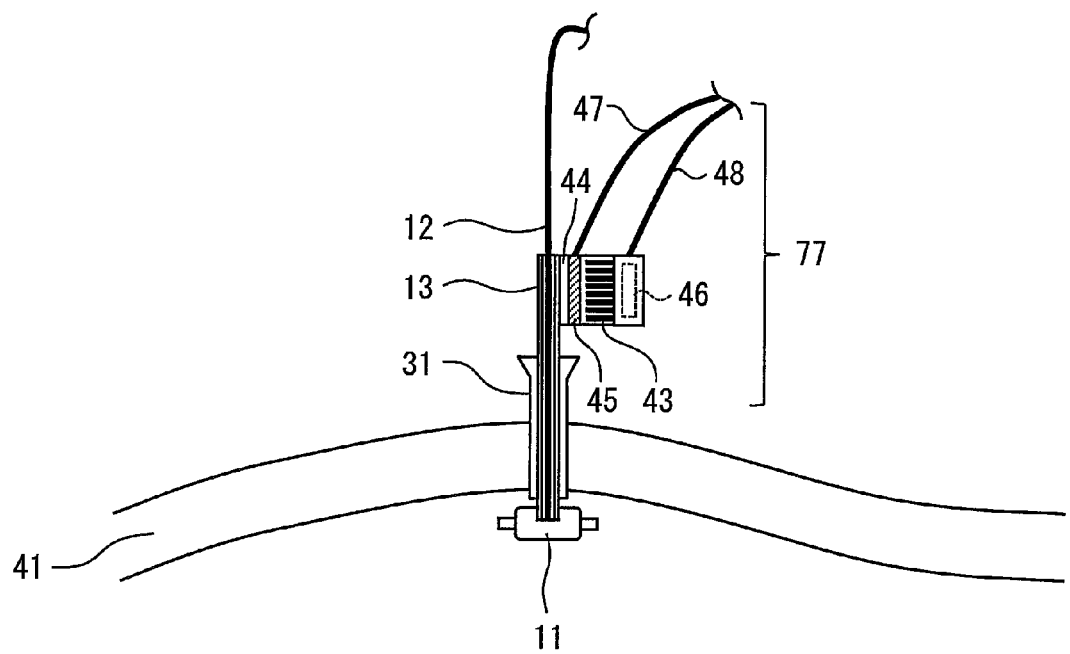
FIG. 10 is a schematic sectional view of a camera unit and a camera support tube according to Embodiment 5.

FIG. 10 is a schematic sectional view of the camera unit 11 and the camera support tube 13 according to Embodiment 5. The low temperature material attaching plate 44 is attached to be in contact with a wide area at a location which is exposed to the outside of the body from the cannula 31 of the camera support tube 13. In addition, a Peltier element 45 is disposed between the heat sink 43 and the low temperature material attaching plate 44. The Peltier element 45 moves the heat which passes through the camera support tube 13 from the camera unit 11 to the heat sink 43. The heat radiation fan 46 is provided in the heat sink 43. The heat radiation fan 46 discharges the heat moved to the heat sink 43 to the air.

The heat generated in the camera unit 11 is transferred to the low temperature material attaching plate 44 through the camera support tube 13. The Peltier element 45 performs heat absorption on the low temperature material attaching plate 44 side, and applies a voltage by Peltier element cables 47 and 48 to cause generation of heat on the heat sink 43 side. In this manner, the heat transferred from the camera support tube 13 is moved to the heat sink 43 from the low temperature material attaching plate 44 by the Peltier element 45. The heat moved to the heat sink 43 is discharged to the air by the heat radiation fan 46 attached to the heat sink 43. Therefore, the heat is efficiently radiated. In this manner, in FIG. 10, the cooling system 77 is configured to include the low temperature material attaching plate 44, the Peltier element 45 (heat radiation amount accelerating unit) which efficiently moves the heat transferred to the low temperature material attaching plate 44 from the camera support tube 13 to the heat sink, the heat sink 43 (heat radiating unit) which discharges the heat from the Peltier element 45 to the air, and a heat radiation fan (heat radiation accelerating unit) which sends the wind to the heat sink 43.

The embodiment illustrates a case where the heat radiation fan 46 is attached to the heat sink 43, but the present invention is not limited thereto. It is possible to cool the heat sink 43 by natural convection without attaching the heat radiation fan 46.

In addition, the cooling system may be configured to send the wind having a room temperature or cool wind having a temperature which is lower than the room temperature, to the part outside the body of the camera support tube, and may be configured to link a cooling apparatus which uses electricity and the camera support tube by a thermal conductor.

[Conclusion]

An in-vivo monitoring camera system 1 according to aspect 1 of the present invention, includes: a support tube (camera support tube 13) of which one end part is introduced into a body; an in-vivo monitoring camera (camera unit 11) which joins with the support tube in the body; a joining portion (support tube joining portion 14) which joins the in-vivo monitoring camera and the support tube to each other; a cable (camera side cable 12) which is connected to the imaging unit, and is drawn out toward the outside of the body through the support tube; a control system (camera unit control instrument 17) which is on the outside of the body, is connected to the cable, and includes at least a display apparatus (display 18); and a heat discharging unit of an in-vivo monitoring camera (low temperature material 40, heat sink 43, heat radiation fan 46) which discharges heat generated from the in-vivo monitoring camera to the outside of the body via the support tube.

According to the configuration, the heat generated from the in-vivo monitoring camera is discharged to the outside of the body via the support tube by the heat discharging unit of an in-vivo monitoring camera. One end part of the support tube is guided toward the inside of the body. Therefore, an effect that it is possible to provide an in-vivo monitoring camera which can efficiently discharge the heat generated inside the in-vivo monitoring camera through the other end part of the support tube, is achieved.

In the in-vivo monitoring camera system 1 according to aspect 2 of the present invention, in the above-described aspect 1, the heat discharging unit of an in-vivo monitoring camera may include a conducted heat absorbing unit (low temperature material 40) which absorbs the heat which is generated from the in-vivo monitoring camera and is conducted to the support tube.

According to the configuration, since the heat which is generated from the in-vivo monitoring camera and is conducted to the support tube is absorbed, it is possible to efficiently discharge the heat generated inside the in-vivo monitoring camera.

In the in-vivo monitoring camera system 1 according to aspect 3 of the present invention, in the above-described aspect 2, the conducted heat absorbing unit may include the low temperature material 40 which absorbs the conducted heat.

According to the configuration, since the heat which is generated from the in-vivo monitoring camera and is conducted to the support tube is absorbed by the low temperature material, it is possible to efficiently discharge the heat generated inside the in-vivo monitoring camera.

In the in-vivo monitoring camera system 1 according to aspect 4 of the present invention, in the above-described aspect 1, the heat discharging unit of an in-vivo monitoring camera may include a heat radiation amount increasing unit (heat sink 43, Peltier element 45, heat radiation fan 46) which increases the heat radiation amount to the air from the support tube.

According to the configuration, since the heat radiation amount to the air of the heat which is generated from the in-vivo monitoring camera and is conducted to the support tube increases, it is possible to efficiently discharge the heat from the in-vivo monitoring camera.

In the in-vivo monitoring camera system 1 according to aspect 5 of the present invention, in the above-described aspect 4, the heat radiation amount increasing unit may include the heat sink 43 which disperses the heat from the support tube.

According to the configuration, since the heat which is generated from the in-vivo monitoring camera and is conducted to the support tube is dispersed by the heat sink, it is possible to efficiently discharge the heat from the in-vivo monitoring camera.

In the in-vivo monitoring camera system according to aspect 6 of the present invention, in the above-described aspect 5, the heat radiation amount increasing unit may further include the heat radiation fan 46 for increasing the movement amount of the air which is in contact with the heat sink.

According to the configuration, since the movement amount of the air which is in contact with the heat sink increases by the heat radiation fan, it is possible to efficiently discharge the heat transferred to the heat sink via the support tube from the in-vivo monitoring camera.

In the in-vivo monitoring camera system according to aspect 7 of the present invention, in the above-described aspect 5, the heat radiation amount increasing unit may further include the Peltier element 45 which is disposed between the heat sink and the support tube, and moves the heat from the support tube to the heat sink.

According to the configuration, since the heat from the support tube moves to the heat sink by the Peltier element, it is possible to efficiently discharge the heat transferred to the support tube from the in-vivo monitoring camera.

In the in-vivo monitoring camera system according to aspect 8 of the present invention, in the above-described aspect 7, the heat radiation amount increasing unit may further include a heat radiation fan for discharging the heat moved to the heat sink to the air.

According to the configuration, since the heat moved to the heat sink is discharged to the air by the heat radiation fan, it is possible to efficiently discharge the heat moved to the heat sink via the support tube and the Peltier element from the in-vivo monitoring camera.

In the in-vivo monitoring camera system according to aspect 9 of the present invention, in the above-described aspect 1, the in-vivo monitoring camera may include an imaging housing which can come into contact with a body wall, and support tube thermal conductivity of a material which configures the support tube may be higher than housing thermal conductivity of a material of the imaging housing.

According to the configuration, since the support tube thermal conductivity of the material which configures the support tube is higher than housing thermal conductivity of the material of the imaging housing, the heat generated from the in-vivo monitoring camera is easily transferred to the support tube for which one end part is guided toward the inside of the body, and it is possible to efficiently discharge the heat via the other end part of the support tube.

In the in-vivo monitoring camera system according to aspect 10 of the present invention, in the above-described aspect 9, the support tube thermal conductivity may be 5 times the housing thermal conductivity.

According to the configuration, since the support tube thermal conductivity is 5 times the housing thermal conductivity, the heat generated from the in-vivo monitoring camera is more easily transferred to the support tube for which one end part is guided toward the inside of the body, and it is possible to more efficiently discharge the heat via the other end part of the support tube.

In the in-vivo monitoring camera system according to aspect 11 of the present invention, in the above-described aspect 1, the in-vivo monitoring camera may include an illumination apparatus which illuminates the inside of the body with light; an imaging element which images the inside of the body illuminated by the illumination apparatus; and a thermal conductor which thermally connects the illumination apparatus, the imaging element, and the joining portion.

According to the configuration, the illumination apparatus, the imaging element, and the joining portion are thermally connected by the thermal conductor. Therefore, the heat generated from the illumination apparatus and the imaging element is easily transferred to the support tube for which one end part is guided toward the inside of the body. As a result, it is possible to efficiently discharge the heat generated from the illumination apparatus and the imaging element via the other end part of the support tube.

In the in-vivo monitoring camera system according to aspect 12 of the present invention, in the above-described aspect 11, thermal resistance between the illumination apparatus and the joining portion, and between the imaging element and the joining portion may be equal to or less than 20° C./W.

According to the configuration, since the thermal resistance between the illumination apparatus and the joining portion, and between the imaging element and the joining portion is equal to or less than 20° C./W, the illumination apparatus, the imaging element, and the joining portion are more thermally connected to each other. Therefore, the heat generated from the illumination apparatus and the imaging element is more easily transferred by the support tube for which one end part is guided toward the inside of the body. As a result, it is possible to more efficiently discharge the heat generated from the illumination apparatus and the imaging element via the other end part of the support tube.

An in-vivo monitoring camera system according to aspect 13, includes: a support tube for which one end part is guided toward the inside of a body; an imaging unit which joins with the support tube in the body; a joining portion which joins the imaging unit and the support tube to each other; a cable which is connected to the imaging unit, and is drawn out toward the outside of the body through the support tube; a control system which is on the outside of the body, is connected to the cable, and includes at least a display apparatus; and a cooling system which cools the support tube to which heat of the imaging unit is transferred.

In the in-vivo monitoring camera system according to aspect 14 of the present invention, in the above-described aspect 13, the cooling system includes a heat absorbing unit which absorbs the heat transferred from the support tube.

In the in-vivo monitoring camera system according to aspect 15 of the present invention, in the above-described aspect 13, the cooling system includes a heat radiating unit which discharges the heat transferred from the support tube to the air.

In the in-vivo monitoring camera system according to aspect 16 of the present invention, in the above-described aspect 15, the cooling system includes a heat radiation accelerating unit which accelerates radiation of the heat to the air by the heat radiating unit.

In the in-vivo monitoring camera system according to aspect 17 of the present invention, in any of the above-described aspects 13 to 16, thermal conductivity of a material which is used for the support tube is higher than thermal conductivity of a material which is used for a housing of the imaging unit.

An in-vivo monitoring camera system according to aspect 18, includes: a support tube for which one end part is guided toward the inside of a body; an imaging unit which joins with the support tube in the body; a joining portion which joins the imaging unit and the support tube to each other; a cable which is connected to the imaging unit, and is drawn out to the outside of the body through the support tube; a control system which is on the outside of the body, is connected to the cable, and includes at least a display apparatus; and a thermal conductor which transfers heat generated in a heat generating member (for example, illumination apparatus, imaging element, control circuit) in the imaging unit to the joining portion.

In the in-vivo monitoring camera system according to aspect 19 of the present invention, in any of the above-described aspects 13 to 18, at least one of the support tube or the joining portion is configured by combining an elastic material and a high thermal conductivity material having higher thermal conductivity than that of a material which is used for a housing of the imaging unit.

In the in-vivo monitoring camera system according to aspect 20 of the present invention, in the above-described aspect 19, the support tube is configured of the high thermal conductivity material having higher thermal conductivity than that of the material which is used for the housing of the imaging unit, and the joining portion is configured by combining the elastic material and the high thermal conductivity material having higher thermal conductivity than that of the material which is used for the housing of the imaging unit.

In the in-vivo monitoring camera system according to aspect 21 of the present invention, in any one of the above-described aspects 13 to 20, the recessed joining portion has a conductive projected part having conductive properties at a bottom part thereof, and when joining the imaging unit and the support tube, an inner circumferential surface of the support tube and the conductive projected part come into contact with each other.

In the in-vivo monitoring camera system according to aspect 22 of the present invention, in the above-described aspect 20, the conductive projected part has a tapered shape when approaching an opening of the joining portion.

In the in-vivo monitoring camera system according to aspect 23 of the present invention, in any one of the above-described aspects 13 to 22, a cable holder which holds and fixes the cable to the support tube is provided, and cable holding strength of the cable holder is greater than joining strength of the support tube and the joining portion.

In the in-vivo monitoring camera system according to aspect 24 of the present invention, in the above-described aspect 23, the joining strength is within a range of from 3 N to 6 N.

In the in-vivo monitoring camera system according to aspect 25 of the present invention, in any one of the above-described aspects 13 to 24, the cable holder which holds and fixes the cable to the support tube is provided, and the cable holding strength of the cable holder is within a range of 5 N to 50 N.

A support tube for an in-vivo monitoring camera system according to aspect of 26 of the present invention, is a support tube for the in-vivo monitoring camera system according to any one of aspects 13 to 25, in which high thermal conductivity material having higher thermal conductivity than that of a material which is used for a housing of the imaging unit is used for each of the support tube and the joining portion, and in which, when joining with the imaging unit, the high thermal conductivity material of the support tube comes into contact with the high thermal conductivity material of the joining portion.

The present invention is not limited to each of the above-described embodiments, various modifications are possible within the range illustrated in claims, and an embodiment which can be obtained by appropriately combining the technical means disclosed in each of different embodiments is also included in the technical range of the present invention. Furthermore, it is possible to form new technical characteristics by combining the technical means disclosed in each of the embodiments.

Industrial Applicability

The present invention can use an in-vivo monitoring camera system which is provided with an in-vivo monitoring camera that can be introduced into the body. In addition, the in-vivo monitoring camera system of the present invention is appropriate for endoscopic surgery.

REFERENCE SIGNS LIST

1 In-Vivo Monitoring Camera System
11 Camera Unit (In-Vivo Monitoring Camera)
12 Camera Side Cable (Cable)
13 Camera Support Tube (Support Tube)
14 Support Tube Joining Portion (Joining Portion)
17 Camera Unit Control Instrument (Control System)
18 Display (Display Apparatus)
21 Camera Housing (Imaging Housing)
27 Illumination Apparatus
25 Solid-State Imaging Element (Imaging Element)
40 Low Temperature Material (Heat Absorbing Unit, Heat Discharging Unit Of In-Vivo Monitoring Camera, Conducted Heat Absorbing Unit)
43 Heat Sink (Heat Radiating Unit, Heat Discharging Unit Of In-Vivo Monitoring Camera, Heat Radiation Amount Increasing Unit)
45 Peltier Element (Heat Radiation Accelerating Unit, Heat Discharging Unit Of In-Vivo Monitoring Camera, Heat Radiation Amount Increasing Unit)
46 Heat Radiation Fan (Heat Radiation Accelerating Unit, Heat Discharging Unit Of In-Vivo Monitoring Camera, Heat Radiation Amount Increasing Unit)
49 Thermal Conductor
77 Cooling System

The invention claimed is:

1. An in-vivo monitoring camera system, comprising:
a support tube for which one end part is introduced into a body;
an imaging unit which joins with the support tube in the body;
a joining portion that is provided in the imaging unit and recessed, and which joins the imaging unit and the support tube to each other;
a cable which is connected to the imaging unit, and is drawn out toward the outside of the body through the support tube; and
a cooling system which cools the support tube to which heat of the imaging unit is transferred; wherein
the imaging unit and the support tube are joined to each other by the support tube being inserted into the joining portion.

2. The in-vivo monitoring camera system according to claim 1,
wherein the cooling system includes a heat absorbing unit which absorbs the heat transferred from the support tube.

3. The in-vivo monitoring camera system according to claim 1,
wherein the cooling system includes a heat radiating unit which discharges the heat transferred from the support tube to the air.

4. The in-vivo monitoring camera system according to claim 3,
wherein the cooling system includes a heat radiation accelerating unit which accelerates radiation of the heat to the outside by the heat radiating unit.

5. The in-vivo monitoring camera system according to claim 1, wherein thermal conductivity of a material which is used for the support tube is higher than thermal conductivity of a material which is used for a housing of the imaging unit.

6. An in-vivo monitoring camera system, comprising:
a support tube for which one end part is introduced into a body;
an imaging unit which joins with the support tube in the body;
a joining portion which joins the imaging unit and the support tube to each other;
a cable which is connected to the imaging unit, and is drawn out toward the outside of the body through the support tube; and
a thermal conductor which transfers heat generated in a heat generating member in the imaging unit to the joining portion; wherein the thermal conductor is provided in a housing of the imaging unit.

7. The in-vivo monitoring camera system according to claim 6, wherein the support tube or the joining portion is configured by combining an elastic material and a high thermal conductivity material having higher thermal conductivity than that of a material which is used for the housing of the imaging unit.

8. The in-vivo monitoring camera system according to claim 7,
wherein the support tube is configured of the high thermal conductivity material having higher thermal conductivity than that of the material which is used for the housing of the imaging unit, and the joining portion is configured by combining the elastic material and the high thermal conductivity material having higher thermal conductivity than that of the material which is used for the housing of the imaging unit.

9. The in-vivo monitoring camera system according to claim 6, wherein the joining portion is recessed and has a conductive projected part having conductive properties at a bottom part thereof, and when joining the imaging unit and the support tube, an inner circumferential surface of the support tube and the conductive projected part come into contact with each other.

10. The in-vivo monitoring camera system according to claim 9,
wherein the conductive projected part has a tapered shape which is tapered off as approaching an opening of the joining portion.

11. The in-vivo monitoring camera system according to claim 6, wherein a cable holder which holds and fixes the cable to the support tube is provided, and cable holding strength of the cable holder is greater than joining strength of the support tube and the joining portion.

12. The in-vivo monitoring camera system according to claim 11,
wherein the joining strength is within a range of from 3 N to 6 N.

13. The in-vivo monitoring camera system according to claim 6, wherein a cable holder which holds and fixes the cable to the support tube is provided, and cable holding strength of the cable holder is within a range of 5 N to 50 N.

14. A support tube for an in-vivo monitoring camera system tube for according to claim 6 in which a high thermal conductivity material having higher thermal conductivity than that of a material which is used for the housing of the imaging unit is used for each of the support tube and the joining portion,
wherein, when joining with the imaging unit, the high thermal conductivity material of the support tube comes into contact with the high thermal conductivity material of the joining portion.

15. The in-vivo monitoring camera system according to claim 6, wherein:
the joining portion is provided in the imaging unit and recessed; and
the imaging unit and the support tube are joined to each other by the support tube being inserted into the joining portion.

* * * * *